US012727837B2

(12) United States Patent
Okumura

(10) Patent No.: US 12,727,837 B2
(45) Date of Patent: Sep. 8, 2026

(54) X-RAY IMAGING APPARATUS AND POSITION DETERMINATION SUPPORT UNIT FOR X-RAY IMAGING APPARATUS

(71) Applicant: SHIMADZU CORPORATION, Kyoto (JP)

(72) Inventor: Hiroshi Okumura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 93 days.

(21) Appl. No.: 18/111,539

(22) Filed: Feb. 18, 2023

(65) Prior Publication Data

US 2023/0277148 A1 Sep. 7, 2023

(30) Foreign Application Priority Data

Mar. 25, 2022 (JP) ................................ 2022-049456

(51) Int. Cl.
*A61B 6/00* (2024.01)
*A61B 6/08* (2006.01)

(52) U.S. Cl.
CPC ............. *A61B 6/4452* (2013.01); *A61B 6/08* (2013.01); *A61B 6/4405* (2013.01)

(58) Field of Classification Search
None
See application file for complete search history.

(56) References Cited

U.S. PATENT DOCUMENTS 9,155,509 B2 10/2015 Lalena et al.
9,760,982 B2 * 9/2017 Luciano .................. G06T 5/92
(Continued)

FOREIGN PATENT DOCUMENTS

CN 102917646 A 2/2013
CN 113271839 A 8/2021
(Continued)

OTHER PUBLICATIONS

Carestream DRX-Revolution, CMX Medical Imaging, https://www.cmxmedicalimaging.com/product/carestream-dx-revolution/, 7 pages, dated Jan. 26, 2023.
(Continued)

*Primary Examiner* — Marcus H Taningco
(74) *Attorney, Agent, or Firm* — Andrew F. Young, ESQ.; NOLTE LACKENBACH SIEGEL

(57) ABSTRACT

An X-ray imaging apparatus has a position determination support unit for that allows adjustment of the relative angular relationship between a detection surface of the X-ray detection element and the irradiation direction of the X-ray of the X-ray irradiation element. The X-ray imaging apparatus has an X-ray irradiation element, an X-ray detection element, an angular relationship detection element that detects the relative angular relationship between the detection surface of the X-ray detection element and the irradiation direction of X-rays of the X-ray irradiation element. A projection element projects the irradiation position marker indicating the position where the X-ray is irradiated from the X-ray irradiation element on a body surface of a subject. The projection element changes the display mode of the irradiation position marker based on the deviation level relative to the preset setting angle of the detected angular relationship.

13 Claims, 13 Drawing Sheets

(56) References Cited

U.S. PATENT DOCUMENTS

| | | | | |
|---|---|---|---|---|
| 10,517,562 | B2 * | 12/2019 | Gu | A61B 6/08 |
| 2006/0269114 | A1 * | 11/2006 | Metz | G06T 11/008 382/131 |
| 2011/0135190 | A1 | 6/2011 | Maad | |
| 2011/0249793 | A1 * | 10/2011 | Lalena | A61B 6/4266 378/62 |
| 2014/0341349 | A1 * | 11/2014 | Lalena | A61B 6/587 378/62 |
| 2021/0338042 | A1 | 11/2021 | Kimura et al. | |
| 2023/0255590 | A1 * | 8/2023 | Talgorn | G09B 23/286 600/407 |

FOREIGN PATENT DOCUMENTS

| | | | |
|---|---|---|---|
| EP | 393513 | A1 | 1/2022 |
| JP | 2013-523396 | A | 6/2013 |

OTHER PUBLICATIONS

Digital Radiography AccE GM85/Samsung Healthcare Global, https://www.samsunghealthcare.com/en/products/DigitalRadiography/Quia, 19 pages, dated Jan. 26, 2023.

China National Intellectual Property Administration, First Office Action in Application No. 202310153714.5, mailed Aug. 15, 2025 (8 pgs CN, 9 pgs EN machine translation).

Japan Patent Office, First Office Action in Application No. 2022-049456, mailed Dec. 9, 2025 (4 pgs JP, 5 pgs EN machine translation).

China National Intellectual Property Administration, Second Office Action in Application No. 202310153714.5, mailed Dec. 2, 2025 (9 pgs CN, 11 pgs EN machine translation).

* cited by examiner

X-RAY IMAGING APPARATUS AND POSITION DETERMINATION SUPPORT UNIT FOR X-RAY IMAGING APPARATUS

CROSS REFERENCE TO RELATED APPLICATIONS

This application relates to and claims priority to Japanese JP 2022-049456 filed Mar. 25, 2022, the entire contents of which are incorporated herein fully by reference.

FIGURE SELECTED FOR PUBLICATION

FIG. 1.

BACKGROUND OF THE INVENTION

Field of the Invention

The present invention relates to an X-ray imaging apparatus and a position determination support unit for the X-ray imaging apparatus and particularly, relates to the X-ray imaging apparatus that detects a detection surface of an X-ray detector and a relative angular relationship between the detection surface and an irradiation direction of an X-ray of an X-ray irradiation element and a position determination support unit for the X-ray imaging apparatus.

Description of the Related Art

It is conventionally known that there is a radiation imaging apparatus detects a relative angular relationship between the radiation pathway (irradiation direction of X-ray) and an imaging surface (detection surface) an image receiver (X-ray detection element) having an X-ray irradiation detection element (e.g., referring to Patent Document 1.)

The radiation imaging apparatus according to the patent document 1 described above has a radiation source, an image receiver, a sensor device, and a display device. According to such a radiation imaging apparatus, the image receiver placed behind a patient forms a diagnostic image from the radiation irradiated from the radiation source. And further according to such a radiation imaging apparatus, the sensor device perceives the relative spatial positional relationship between the radiation source and the image receiver and also the display device generates an image denoting the alignment of the image receiver relative to the radiation pathway. According to the radiation imaging apparatus according to the patent document 1 described above, the display device displays a center position (centering) of the image receiver relative to the radiation pathway, an angle of the radiation pathway relative to the imaging surface of the image receiver and the SID (Source to Image receptor Distance) to align the positions of the radiation source relative to the image receiver.

According to the radiation imaging apparatus according to the patent document 1 described above, the display device includes a projector to project the image supporting position alignment. Such a projector projects the image receiver pattern, specifying the position of the image receiver, on a patient. The radiation imaging apparatus according to the patent document 1 described above, has a collimator light source that projects the collimator pattern specifying the irradiation range of the radiations. And such a radiation imaging apparatus that is configured to enable the position alignment of irradiation range of the radiations relative to the image receiver by adjusting the position of the radiation source using the collimator pattern from the collimator light source and the image receiver pattern from the projector. Further, the projector is configured to project the numeric value of angle of the radiation pathway relative to the image receiver and the SID numeric value.

RELATED PRIOR ART

PATENT DOCUMENT Patent Document 1 U.S. Pat. No. 9,155,509.

ASPECTS AND OBJECTS OF THE INVENTION

Objects to be Solved

According to the radiation imaging apparatus according to the patent document 1 described above, however, it must be decided whether the angle of the direction of the X-ray irradiation (the relative angular relationship between the detection surface of the X-ray detection element and the irradiation direction of the X-ray) is included within an adequate range or not by confirming the projected numeric value while adjusting the position where the X-ray is irradiated by confirming the image receiver pattern specifying the position of the projected X-ray detection element. In this case, the projected numeric value must be confirmed, so that whether the angular relationship is included in the adequate range or not cannot be intuitively recognized. Therefore, it has been expected that the adjustment of the relative angular relationship between the detection surface and the irradiation direction of the X-ray from the X-ray irradiation element is carried out easily in addition to adjusting the position where the X-ray is irradiated by intuitively recognizing the angular relationship.

The present invention has been proposed in order to solve the aforementioned problems, and an object of the present invention is to provide an X-ray imaging apparatus and a position determination support unit for the X-ray imaging apparatus that are capable of easily carrying out adjustment of the relative angular relationship between the detection surface of the X-ray detection element and the irradiation direction of the X-ray of the X-ray irradiation element in addition to adjustment of the position where the X-ray is irradiated.

Means for Solving the Problem

To achieve the above purpose, the X-ray image imaging apparatus according to the first aspect of the present invention comprises: an X-ray irradiation element that irradiates an X-ray to a subject; an X-ray detection element that detects the X-ray irradiated from the X-ray irradiation element; an angular relationship detection element that detects relative angular relationship between the detection surface of the X-ray detection element and the irradiation direction of the X-ray of the X-ray irradiation element; and a projection element that projects the irradiation position marker specifying the position where the X-ray is irradiated from the X-ray irradiation element on the body surface of the subject, wherein the projection element changes the display mode for the irradiation position marker based on the deviation level relative to the preset angle of the angular relationship detected by the angular relationship detection element. In addition, the "body surface of the subject" represents a broad concept including not only the skin surface of the subject but also the surface of clothes that the subject is wearing.

The position determination support unit for the X-ray imaging apparatus according to the second aspect of the present invention comprises: an angular relationship detection element that detects an angular relationship between the X-ray irradiation direction of the X-ray from the X-ray irradiation element that irradiates X-ray to the subject, and a projection element that projects the irradiation position marker specifying the position where the X-ray is irradiated from the X-ray irradiation element on the body surface of the subject, wherein the projection element is configured to change the display mode for the irradiation position marker based on the deviation level corresponding to the preset angle of the angular relationship detected by the angular relationship detection element.

Effects of the Present Invention

The X-ray imaging apparatus according to the first aspect described above and the position determination support unit for the X-ray imaging apparatus according to the second aspect described above have the projection element that projects the irradiation position marker specifying the irradiation position where the X-ray is irradiated from the X-ray irradiation element on the body surface of the subject. And the projection element changes the display mode of the irradiation position marker based on the deviation level relative to the preset angle of the angular relationship detected by the angular relationship detection element. Therefore, the irradiation position marker is projected on the body surface of the subject by the projection element, so that the adjustment of the position where the X-ray is irradiated can be easily carried out by confirming the irradiation position marker. And the display mode of the projected irradiation position marker is changed based on the deviation level of the angular relationship, so that whether the angular relationship is included in the adequate range or not can be intuitively recognized by visually confirming the irradiation position marker differently from the case in which the project numeric value must be confirmed. Consequently, the adjustment of the relative angular relationship between the detection surface and the irradiation direction of the X-ray of the X-ray irradiation element is carried out easily in addition to adjusting the position where the X-ray is irradiated.

The above and other aspects, features, objects, and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
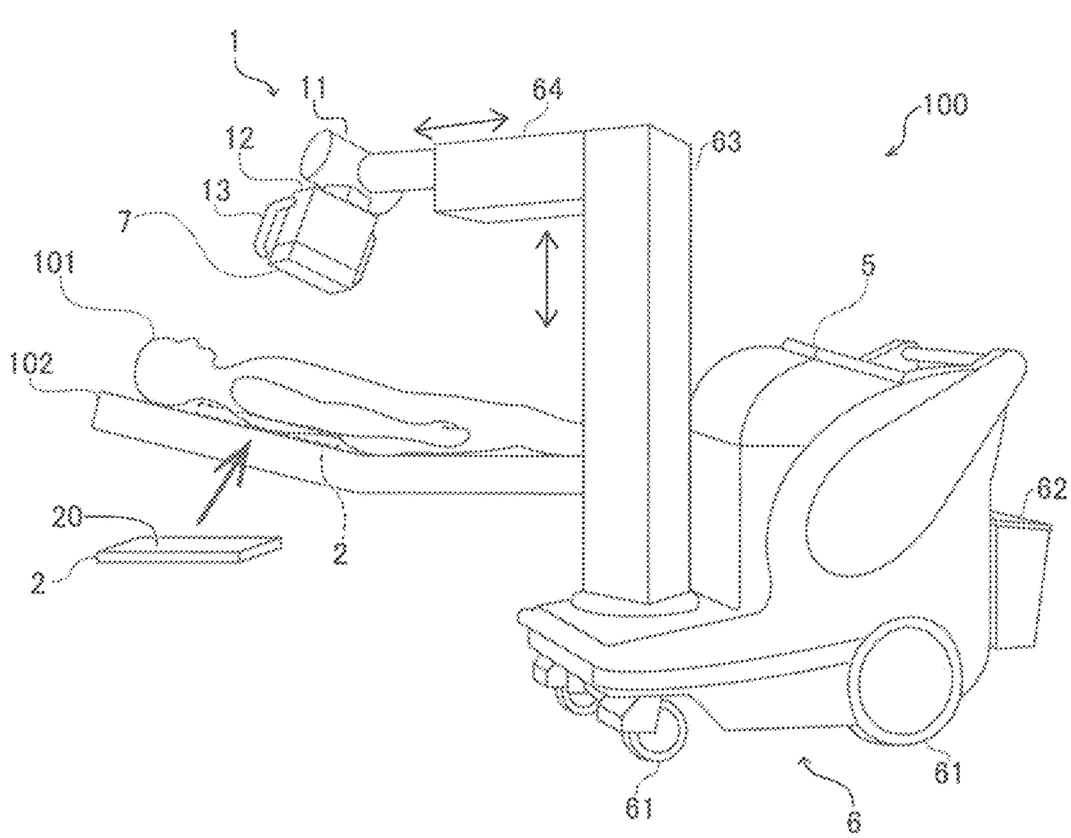
FIG. 1 is a schematic view illustrating a configuration of an X-ray imaging apparatus according to the aspect of the Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Embodiment 1

Configuration of an X-Ray Imaging Apparatus

Referring to FIG. 1 to FIG. 7, the inventor sets forth the X-ray imaging apparatus 100 according to the aspect of the Embodiment 1 of the present invention.

Figure 2:
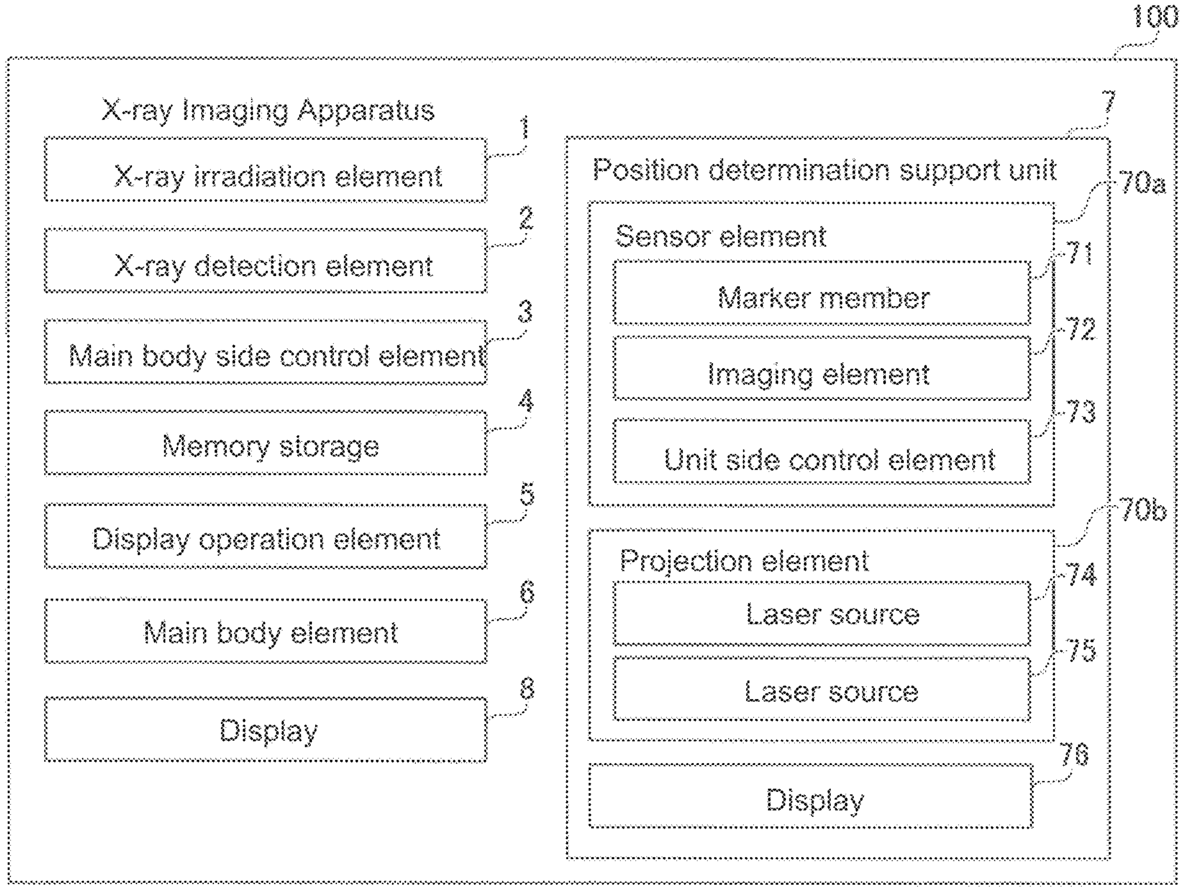
FIG. 2 is a block diagram illustrating the configuration of the X-ray imaging apparatus according to the aspect of the Embodiment 1.

Referring to FIG. 1 and FIG. 2, the X-ray imaging apparatus 100 is the entire of the apparatus is a portable and movable X-ray imaging apparatus. The portable (mobile) X-ray imaging apparatus 100 is designed to be capable of being moved and carrying out the X-ray imaging where the patient (subject 101) has been lying on the bed 102 in each patient room of the medical facility while visiting each patient room.

Further, the X-ray imaging apparatus 100 comprises: an X-ray irradiation element 1; an X-ray detection element 2; a main body side control element 3; a memory storage 4; a display operation element 5; a main body element 6; a position determination support unit 7, and a display 8. In addition, the position determination support unit 7 is an example of the position determination support unit for the X-ray imaging apparatus claimed in Claims.

The X-ray irradiation element 1 irradiates an X-ray toward a subject 101. The X-ray irradiation element 1 further comprises an X-ray tube 11, a collimator 12 and a grip 13. The X-ray tube 11 irradiates X-ray when voltage is added by the electric power equipment. The collimator 12 adjusts the X-ray irradiation field (irradiation area) of X-rays irradiated toward the subject 101. The grip 13 is fixed to the collimator 12 and is held by an operator such as a medical doctor or a radiologic technologist when changing the position of the X-ray irradiation element 1.

The X-ray detection element 2 detects the X-ray irradiated from the X-ray irradiation element 1 followed by transmitting through the subject 101. The X-ray detection element 2 includes, e.g., a FPD (flat panel detector). The X-ray detection element 2 outputs a detection signal based on the detected X-ray. Further, the X-ray detection element 2 is configured to be a wireless X-ray detector and outputs the detection signal as a wireless signal. Specifically, the X-ray detection element 2 is communicable with a control element for the main body side 3, described later, by the wireless connection such as a wireless LAN, so that the detection signal can be output as the wireless signal to the main body side control element 3. Further, the X-ray detection element 2 is in the form of plates and in place between the subject 101 and the bed 102 where the subject 101 is lying while the X-ray is being irradiated (when conducting the X-ray imaging). Further, the X-ray detection element 2 has a detection surface 20 in the side where the X-ray is irradiated (X-ray irradiation element side 1). And the X-ray detection element 2 is stored in the housing 62, described later, of the main body unit 6 when not-in-use for the X-ray imaging.

The main body side control element 3 carries out controlling the X-ray imaging by controlling the X-ray irradiation element 1 and the X-ray detection element 2. Further, the main body side control element 3 is communicable with the X-ray detection element 2 with the wireless connection such as the wireless LAN. And the main body side control element 3 generates an X-ray image based on the X-ray detection signal detected by the X-ray detection element 2. The main body side control element 3 is a computer consisting of such as a CPU (central processing unit), a GPU (graphics processing unit), a ROM (read only memory) and a RAM (random access memory).

The memory storage element 4 comprises a memory device such as, e.g., a hard disk drive. The memory storage element 4 stores image data such as generated X-ray images. Further, the memory element 4 is designed to store a variety of a setting value to run the X-ray imaging apparatus 100. Further, the memory storage element 4 stores a computer program used for control processing of X-ray imaging apparatus 100 by the main body side control element 3.

The display operation element 5 includes, e.g., a liquid crystal display operative as a touch panel. And the display operation element 5 is operative as a display that displays the X-ray image generated by the X-ray imaging and the imaging order information and as an input element to which a variety of operations is input by the operator such as the medical doctor or the radiologic technologist.

The main body element 6 is a wheeled platform of the X-ray imaging apparatus 100 and includes such as a power source and a battery, not shown in FIG., in the inside thereof. Further, main body side control element 3 and the memory storage element 4 are housed in the inside of the main body element 6. Further, a plurality of wheels 61, the housing 62, a support column 63 and the arm element 64 are installed to the main body element 6. A plurality of the wheels 61 is installed under the main body element 6 for moving the main body element 6. Further, the housing 62 is installed to the rear part of the main body element 6. The housing 62 is designed to store the X-ray detection element 2 capable of being drawn out therefrom.

Further, the support column 63 is vertically installed in an anterior section of the main body element 6. And the arm element 64 is installed so as to be extending from the support column 63 in the horizontal direction. Further, the support column 63 is rotatable in the horizontal direction. Further, the inside of the support column 63 is hollow and the components capable of lifting the arm element 64 are housed in the inside thereof. And the arm element 64 is mounted on the movable X-ray irradiation element. Further, the arm element 64 is movable up-and-down relative to the support column 63 and contractible to enable changing the horizontal position of the X-ray irradiation element 1. Specifically, the X-ray irradiation element 1 is movable in the vertical direction along with moving the arm element 64 up-and-down and also in the horizontal direction along with rotation and expansion-and-contraction of the arm element 64. And the X-ray irradiation element 1 mounted on the arm element 64 enables changing the irradiation angle of the X-ray.

And when the X-ray imaging apparatus 100 conducts the X-ray imaging for the subject, the operator such as the medical doctor or the radiologic technologist places the X-ray detection element 2 between the subject 101 and the bed 102 and moves the X-ray irradiation element 1. In the state in which the X-ray irradiation element 1 is in place so that the irradiation direction of the X-ray becomes orthogonal to the detection surface 20 of the X-ray detection element 2, the operator aligns the position (position determination) so that the irradiation center of the irradiated X-ray becomes the center position of the detection surface 20 of the X-ray detection element 2.

Position Determination Support Unit

Here, when the irradiation direction of the X-ray is deviated from the orthogonal direction to the detection surface 20, the level of visual recognition of the generated X-ray image lowers. For example, when the irradiation direction of the X-ray is deviated to either right or left direction of the subject 101 when conducting an X-ray imaging for lungs, each size of the right lung and the left lung in the X-ray image is different from the other. Further, when the irradiation direction of the X-ray is deviated in the direction toward the head of the subject 101, the visual recognition of the apical portion of the lung lowers due to overlapping of the apical portion of the lung located at the upper portion of the lung and the clavicle in the X-ray image. Further, given multiple X-ray imaging are conducted for the subject for the subject 101, the further accurate relative position determination between the X-ray irradiation element 1 and the X-ray detection element 2 is needed to keep consistency. Then, according to the aspect of the Embodiment 1, the position determination support unit 7 that supports the position determination of the X-ray irradiation element 1 by the operator is mounted on the X-ray imaging apparatus 100.

Referring to FIG. 2, the position determination support unit 7 includes the sensor element 70*a* and the projection element 70*b*. The sensor element 70*a* includes the marker member 71, the imaging element 72 and the unit side control element 73. Further, the projection element 70*b* includes the laser source 74 and the laser source 75. Further, the position determination support unit 7 includes the display 76. In addition, the sensor element 70*a* is an example of an "angular relationship detection element" and a "positional relationship detection element" in Claims. Further, the unit side control element 73 is an example of a "control element" in Claims.

The position determination support unit 7 is applied to the X-ray imaging apparatus 100 having the X-ray irradiation element 1 and the X-ray detection element 2. In the position determination support unit 7, the three-dimensional arrangement (position and angle) of the X-ray detection element 2 for the X-ray irradiation element 1 is detected by the sensor element 70*a*. And the display supporting positioning (position determination) of the X-ray irradiation element 1 is projected on the body surface of the subject 101 by the projection element 70*b*.

Detection of the Position and the Angle

Figure 3:
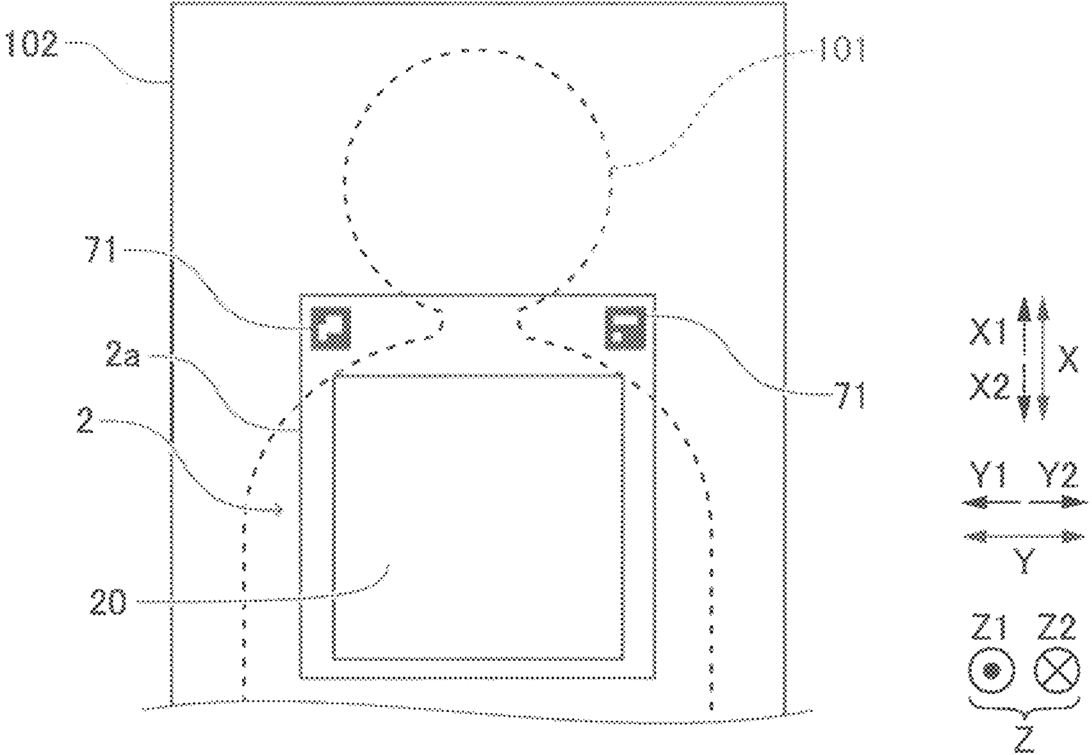
FIG. 3 is a schematic diagram illustrating the X-ray detection element and the marker member.
Figure 4:
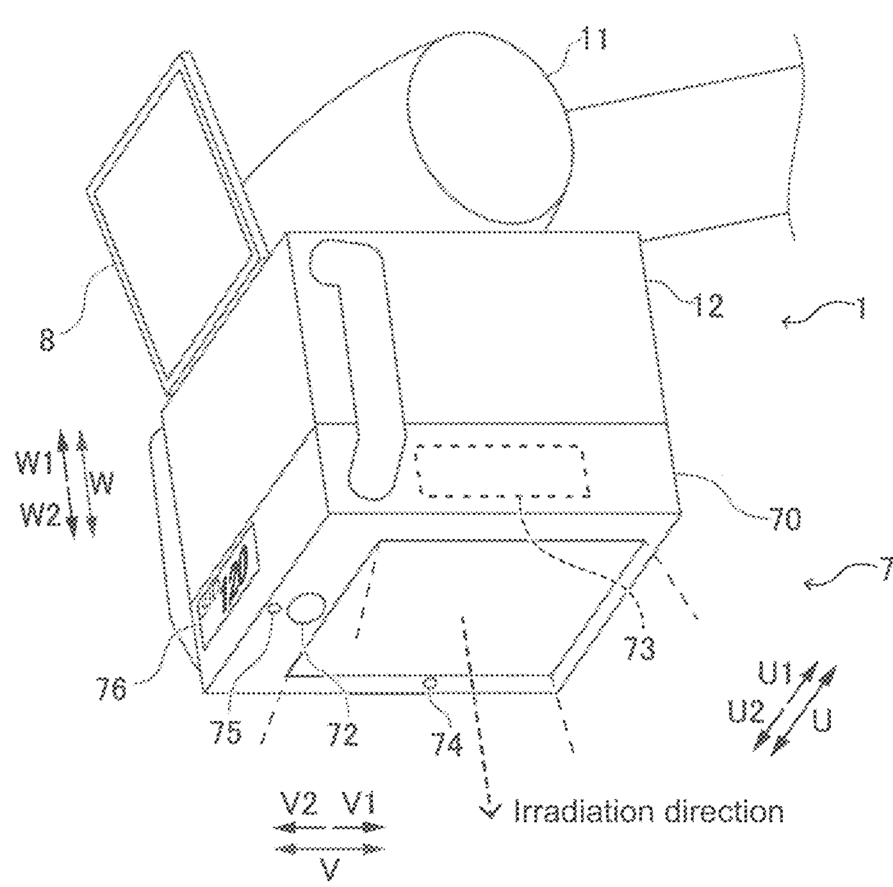
FIG. 4 is a schematic view illustrating the position determination support unit for the X-ray imaging apparatus according to the aspect of the Embodiment 1.
Figure 5:
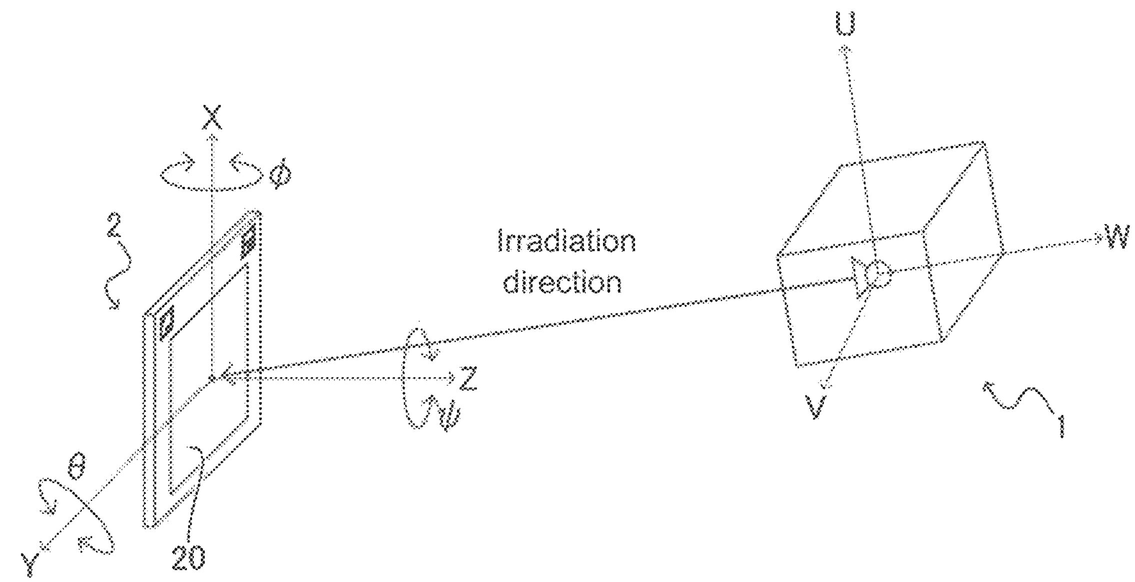
FIG. 5 is a schematic view illustrating the sensor element detecting the relative positional relationship and the angular relationship.

Specifically, referring to FIG. 3 to FIG. 5, the sensor element 70*a* according to the aspect of the Embodiment 1 detects the relative angular relationship between the detection surface 20 of the X-ray detection element 2 and the irradiation direction of the X-ray of the X-ray irradiation element 1. Further, the sensor element 70*a* detects the relative position relationship between the X-ray irradiation element 1 and the X-ray detection element 2. Specifically, the sensor element 70*a* detects the relative position and angle between the X-ray irradiation element 1 and the X-ray detection element 2 by detecting the marker member 71 installed to the X-ray detection element 2. In addition, the X-direction, the Y-direction and the Z-direction in FIG. 3 denote the direction based on the X-ray detection element 2, and the U-direction, the V-direction and the W-direction is the direction based on the X-ray irradiation element 1.

Referring to FIG. 3, the marker member 71 is in place at the corner portion of the cover member 2*a* of the X-ray detection element 2. Each marker member 71 is, for example, installed to each corner of two corner portions of four corners of the X-ray detection element 2 in the X1-direction side. The marker member 71 is installed as the member separable from the X-ray detection element 2 and arranged as demountable therefrom. Further, the marker member 71 has a rectangular shape.

The marker member 71 is so to speak an AR marker, wherein the information obtainable by being imaged by the imaging element 72 is preset. The marker member 71 is arranged so as to be recognizable from the imaging element 72 (Z1-direction side) in the cover member 2*a* in the state in which the X-ray detection element 2 is in place between the subject 101 and the bed 102. For example, when the X-ray imaging for the lung of the subject 101 is carried out, the marker member 71 is positioned at the upper side (X1-direction) than the shoulder of the subject 101 while the detection surface 20 of the X-ray detection element 2 is positioned at the backside of the subject 101 lying face up.

Referring to FIG. 4, the imaging element 72 and the unit-side control element 73 are in place in the X-ray irradiation element 1. Specifically, in the collimator 12 of the X-ray irradiation element 1, the unit housing element 70 of the position determination support unit 7 is in place in the irradiation direction side (subject 101 side, W2-direction side) in which the X-ray is irradiated. In the unit housing element 70, a rectangular opening through which the irradiated X-ray transmits is installed in the irradiation side of the collimator 12. Such an opening has a rectangular shape of which each side is along the U-direction and the V-direction in the irradiation direction side of the unit housing element 70. And the imaging element 72 and the unit-side control element 73 are in place in the unit housing element 70.

The imaging element 72 of the irradiation direction side (W2-direction side) of the unit housing element 70 of the position determination support unit 7 is in place near the center in the U-direction and at the V2-direction side of the opening. And the imaging element 72 optically images the subject 101 side (W2-direction side) along the irradiation direction of the X-ray from the X-ray irradiation element 1 side. According to the aspect of the Embodiment 1, the imaging element 72 optically images the marker member 71 to detect the three-dimensional arrangement (position and angle) of the X-ray detection element 2. The imaging element 72 images the image taken as a video and outputs the taken image to the unit side control element 73. The imaging element 72 includes, e.g., a CCD (charge coupled device) image sensor or a CMOS (complementary metal oxide semiconductor) image sensor.

The unit side control element 73 executes a control of each element of the position determination support unit 7. The unit side control element 73 executes controls of imaging by the imaging element 72, the projection of the irradiation position marker 90 (referring FIG. 6), described later, by the projection element 70*b* and the display of the display 76. Further, the unit side control element 73 executes a control of the display of the display 8 described later. Further, the unit side control element 73 is the computer consisting of, e.g., CPU, ROM, RAM and the memory device such as a flash memory.

Specifically, according to the aspect of the Embodiment 1, the unit side control element 73 detects the relative positional relationship between the irradiation element 1 and the X-ray detection element 2 and the relative angular relationship between the detection surface 20 of the X-ray detection element 2 and the irradiation direction (W2-direction) of the X-ray of the X-ray irradiation element 2 based on the marker member 71 imaged by the imaging element 72. In detail, the unit side control element 73 obtains the three-dimensional position information of the marker member 71 and the angle information in the imaged image by detecting the marker member 71 among the imaged images taken by the imaging element 72. Further, the unit side control element 73 preliminarily stores the information of such as the size and shape of the marker member 71, the information of the positional relationship of the marker member 71 relative to the X-ray detection element 2, and the information of the positional relationship of the imaging element 72 relative to the X-ray irradiation element 1 as parameters for the detection processing. And the unit side control element 73 is configured to detect the relative positional relationship and the angular relationship between the X-ray irradiation element 1 and the X-ray detection element 2 based on the position information of the marker member 71 detected in the imaged image and the preliminarily stored parameters for the detection processing.

Referring to FIG. 5, the unit side control element 73 is configured to detect the three-dimensional positional relationship between the X-ray irradiation element 1 and the X-ray detection element 2. The unit side control element 73 is configured to detect an X-ray focus, which is the relative positional relationship of the X-ray detection element 2 (detection surface 20) for the X-ray tube 11, as to each of the triaxial direction of the longitudinal axis direction (X-direction) of the detection surface 20, the horizontal axis direction (Y-direction), and the orthogonal direction (Z-direction) orthogonal to the detection surface 20.

Further, the unit side control element 73 detects the relative angular relationship between the irradiation direction (W2-direction) of the X-ray of the X-ray irradiation element 1 and the detection surface 20 of the X-ray detection element 2 as to each of three rotation angle directions. For example, the unit side control element 73 detects the relative angular relationship as to each of the roll angle direction (φ-direction) when the longitudinal axis direction of the detection surface 20 is the rotation axis, the pitch angle direction (θ-direction) when the horizontal axis direction (Y-direction) is the rotation axis, and the yaw angle direction (ψ-direction) when the orthogonal direction (Z-direction) is the rotation axis. In addition, the roll angle direction (φ-direction) is one example of the first rotation direction in Claims. Further, the pitch angle direction (φ-direction) is the second rotation direction in Claims. Further, the yaw angle direction (ψ-direction) is the third rotation direction in Claims.

Projection of the Irradiation Position Marker

Referring to FIG. 4, the laser source 74 of the projection element 70*b* and the laser source 75 are in place in the unit housing element 70 of the position determination support unit 7. Specifically, the laser source 74 is in place near the center in the V-direction of the opening at the U2-direction side of the irradiation direction side (W2-direction side) of the unit housing element 70 of the position determination support unit 7. The laser source 75 is in place near the center in the U-direction of the opening as adjacent to the imaging element 72 at the V2-direction side of the irradiation direction side (W2-direction side) of the unit housing element 70 of the position determination support unit 7. The laser sources 74 and 75 include, for example, a laser diode and the lens member that diffuses the laser light from the laser diode as a sheet-like (plan-like) aspect.

Figure 6:
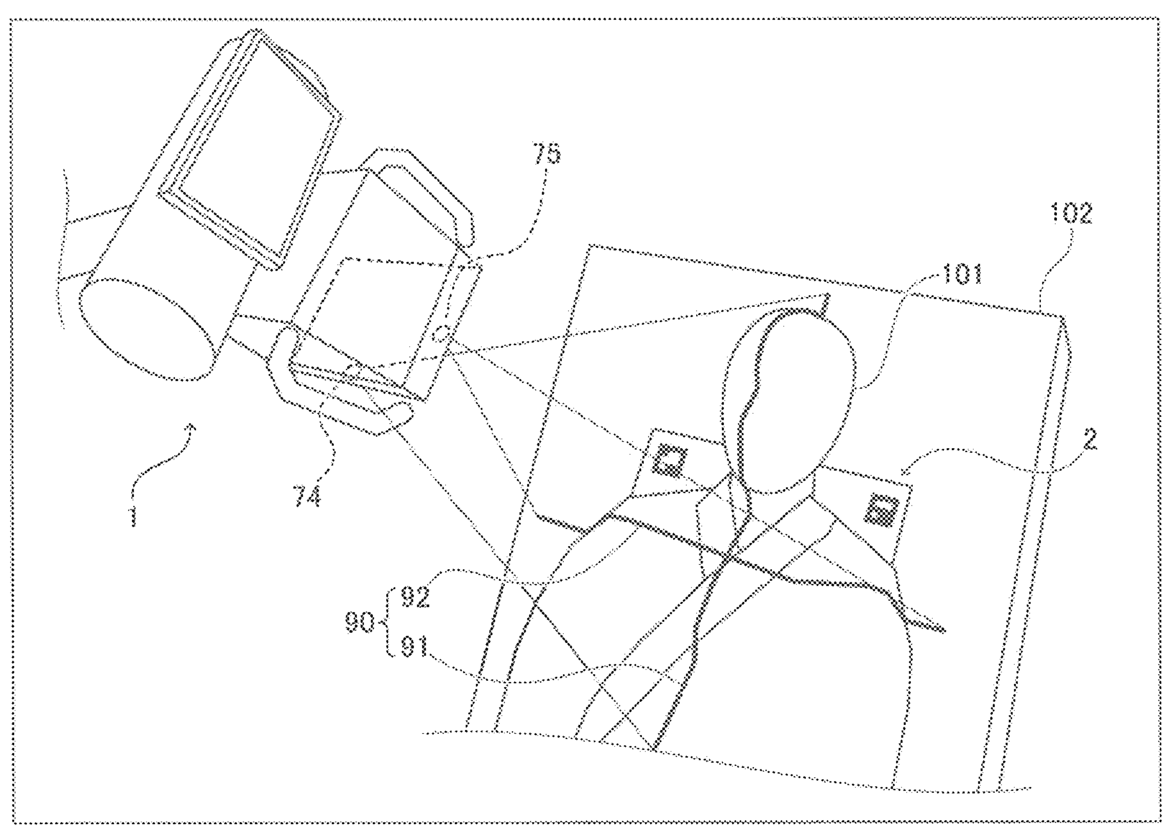
FIG. 6 is a schematic view illustrating the projection element projecting the irradiation position marker.

Referring to FIG. 6, according to the aspect of the Embodiment 1, the laser source 74 and the laser source 75 of the projection element 70*b* project the irradiation position marker 90 specifying the position, on the body surface of the subject 101, where the X-ray is irradiated from the X-ray irradiation element 1. The irradiation position marker 90 indicates the irradiation center of the X-ray irradiated from the X-ray irradiation element 1. Specifically, the laser source 74 and the laser source 75 of the projection element 70*b* are configured to project the cruciform cross shape) irradiation position marker 90 by respectively projecting the linear first projection light 91 and linear second projection light 92 orthogonal each other on the body surface of the subject 101. The cruciform intersection of the irradiation position marker 90 indicates the irradiation center position where the X-ray from the X-ray irradiation element 1. Specifically, the laser source 74 irradiates the first projection light 91, which is the laser light that diffuses in the sheet-like aspect along the U-direction, toward the W2-direction side. Further, and the laser source 75 irradiates the second projection light 92, which is the laser light that diffuses in the sheet-like aspect along the V-direction toward the W2-direction side.

Further, the projection element 70*b* (laser source 74 and 75) is configured to project the irradiation position marker 90 based on the control signal from the unit side control element 73. According to the aspect of the Embodiment 1, the angle around the yaw angle direction (ψ-direction) of the X-ray irradiation element 1 is adjusted by that the operator adjusts the angle of the X-ray irradiation element 1 while visually recognizing the first projection light 91 and the second projection light 92 projected on the body surface of the subject 101 so that the first projection light 91 is projected linearly along the X-direction of the detection surface 20 and also the second projection light 92 is projected linearly along the Y-direction of the detection surface 20.

Projection of the Irradiation Position Marker

Here, the unit side control element 73 is configured to let the projection element 70*b* (laser source 74 and laser source 75) project the irradiation position marker 90 and change the display mode of the irradiation position marker 90 so as to notify the angle deviation when the relative angular relationship of the irradiation direction of the X-ray relative to the detection surface 20 deviates from the preset setting angle.

Specifically, the unit side control element 73 detects the relative angular relationship between the irradiation direction of the X-ray of the X-ray irradiation element 1 and the detection surface 20 of the X-ray detection element 2 and also calculates the deviation level of the angular relationship relative to the preset setting angle based on the detected angular relationship. In detail, the unit side control element 73 calculates respectively the roll angle deviation level that is the deviation level to the setting angle of the angular relationship in the roll angle direction (φ-direction) of the X-ray detection element 2 and the pitch angle deviation level that is the deviation level to the setting angle of the angular relationship in the pitch angle direction (θ-direction). In addition, the roll angle deviation level is an example of "the first deviation level" in Claims. In addition, the pitch angle deviation level is an example of "the second deviation level" in Claims.

In addition, according to the aspect of the Embodiment 1, the setting angle is set as the orthogonal angle that is the angular relationship in which the irradiation direction of the X-ray of the X-ray irradiation element 1 is orthogonal to the detection surface 20 of the X-ray detection element 2. Specifically, the angular relationship, in which the irradiation direction (W2-direction) of the X-ray irradiation element 1 is facing along the orthogonal direction (Z-direction) orthogonal to the detection surface 20, is preliminarily set as setting angle. The setting angle is stored in, e.g., the memory device of the unit side control element 73.

And according to the aspect of the Embodiment 1, the unit side control element 73 is configured to change the display mode of the irradiation position marker 90 projected by the projection element 70*b* based on the calculated deviation level of the angular relationship (the roll angle deviation level and the pitch angle deviation level). Specifically, according to the aspect of the Embodiment 1, the projection element 70*b* (the laser source 74 and the laser source 75) is configured to change the display mode of the irradiation position marker 90 by switching the irradiation position marker 90 between the display (display-mode) and the non-display (non-display-mode) according to the control by the unit side control element 73 based on the deviation level from the setting angle (orthogonal angle) of the angular relationship between the detection surface 20 and irradiation direction (W2-direction).

In detail, the unit side control element 73 stores the angle deviation threshold value preliminarily set. And the unit side control element 73 suspends the projection of the irradiation position marker 90 when the calculated deviation level of the angular relationship is larger than the angle deviation threshold value. Specifically, the projection element 70*b* turns the irradiation position marker 90 to the non-display when the deviation level is larger than the angle deviation threshold value. And the unit side control element 73 projects the irradiation position marker 90 when the calculated deviation level is smaller than the angle deviation threshold value. Specifically, the projection element 70*b* turns the irradiation position marker 90 to the display when the deviation level is smaller than the angle deviation threshold value. The angle deviation threshold value is, e.g., 4 degrees. Further, the angle deviation threshold value is preliminarily stored in the memory device of the unit side control element 73.

Here, according to the aspect of the Embodiment 1, the projection element 70*b* is configured to change individually the display mode of the irradiation position marker 90 corresponding to the roll angle deviation level and the display mode of the irradiation position marker 90 corresponding to the pitch angle deviation level so that each of the roll angle deviation level and the pitch angle deviation level becomes individually distinguishable. Specifically, according to the aspect of the Embodiment 1, the unit side control element 73 changes the display mode of the first projection light 91 from the laser source 74 of the projection element 70*b* based on the roll angle deviation level. And the unit side control element 73 changes the display mode of the second projection light 92 from the laser source 75 of the projection element 70*b* based on the pitch angle deviation level.

Specifically, the units control element 73 turns the first projection light 91 projected in the X-direction, i.e., along the rotation axis of the roll angle direction (φ-direction), to the non-display when the roll angle deviation level is larger than the angle deviation threshold value. And the unit side control element 73 displays the first projection light 91 when the roll angle deviation level is smaller than the angle deviation threshold value. Also, the units control element 73 turns the second projection light 92 projected in the Y-direction, i.e., along the rotation axis of the pitch angle direction (θ-direction), to the non-display when the pitch angle deviation level is larger than the angle deviation threshold value. And the unit side control element 73 displays the second projection light 92 when the pitch angle deviation level is smaller than the angle deviation threshold value.

For example, referring to FIG. 6, when the X-ray is irradiated in the front to the chest of the subject 101 and the irradiation axis (irradiation direction) of the X-ray is shifted in the right or left direction (roll angle direction) of the subject 101, the first projection light 91 projected along the cephalocodal direction, i.e., from head to tail direction of the subject 101 becomes the non-display. And when the irradiation axis of the X-ray is deviated in the head-to-tail direction (pitch angle direction), the second projection light 92 projected along the right-to-left direction of the subject 101 becomes the non-display.

Representation of the Display

Referring to FIG. 4, the display 76 is installed to the side plane of the V2-direction side of the unit housing element 70 of the position determination support unit 7. The unit side control element 73 displays the representation denoting the SID (source to image receptor distance) on the display 76. Specifically, the unit side control element 73 calculates SID based on the detected three-dimensional position relationship between the X-ray irradiation element 1 and the X-ray detection element 2. And the unit side control element 73 displays the calculated numeric value of the SID on the display 76. The display 76 is, e.g., an organic EL display.

Further, the X-ray imaging apparatus 100 comprises the display 8 separately from the display 76. The display 8 is installed to the upper part (W1-direction side) of the collimator 12 of the X-ray irradiation element 1 The display 8 is, e.g., a liquid crystal display. The display 8 connects with the unit side control element 73 through a cable, not shown in FIG.

Figure 7:
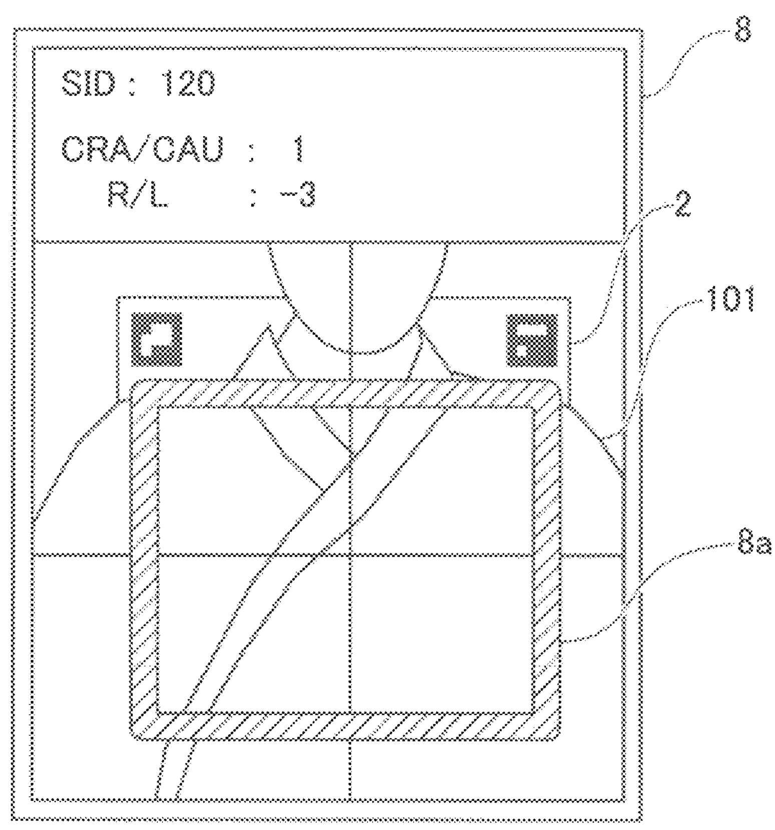
FIG. 7 is a schematic view illustrating one display example on the display installed to the collimator.

Referring to FIG. 7, the unit side control element 73 displays the imaged image taken by the imaging element 72, the specific numeric value of the detected angle related deviation levels (roll angle deviation level and pitch angle deviation level), and the numeric value of SID on the display 8. In addition, referring to FIG. 7, R/L denotes the roll angle deviation level in the right and left direction of the subject 101 as an angle, and CRA/CAL denotes the pitch angle deviation level in the head-to-tail direction of the subject 101 as an angle. Further, the unit side control element 73 displays the imaged image taken by the imaging element 72 on the display 8 and also the detection region display 8*a* superimposed on the imaged image. The unit side control element 73 calculates the region where the X-ray is detected by the X-ray detection element 2 based on the position information of the marker member 71 detected in the imaged image. And the unit side control element 73 displays the detected region of the X-ray on the detection surface 20 of the X-ray detection element 2 in the imaged image as the detected region display 8*a*. The detected region display 8*a* is displayed, e.g., as the green frame line surrounding the detected region of the X-ray.

In addition, the unit housing element 70 of the position determination support unit 7 is configured to be demountable (mountable later) relative to the X-ray irradiation element 1. Specifically, according to the aspect of the Embodiment 1, the imaging element 72, the unit side control element 73, and the laser sources 74 and 75 of the projection element 70*b* are configured to be demountable on the X-ray irradiation element 1. Accordingly, the position determination support unit 7 is configured to be mountable later on the existing x-ray imaging apparatus 100. Further, the display 8 as well as the position determination support unit 7 is also configured to be demountable on the X-ray irradiation element 1 (mountable later).

Method of Supporting the Position Determination

Figure 8:
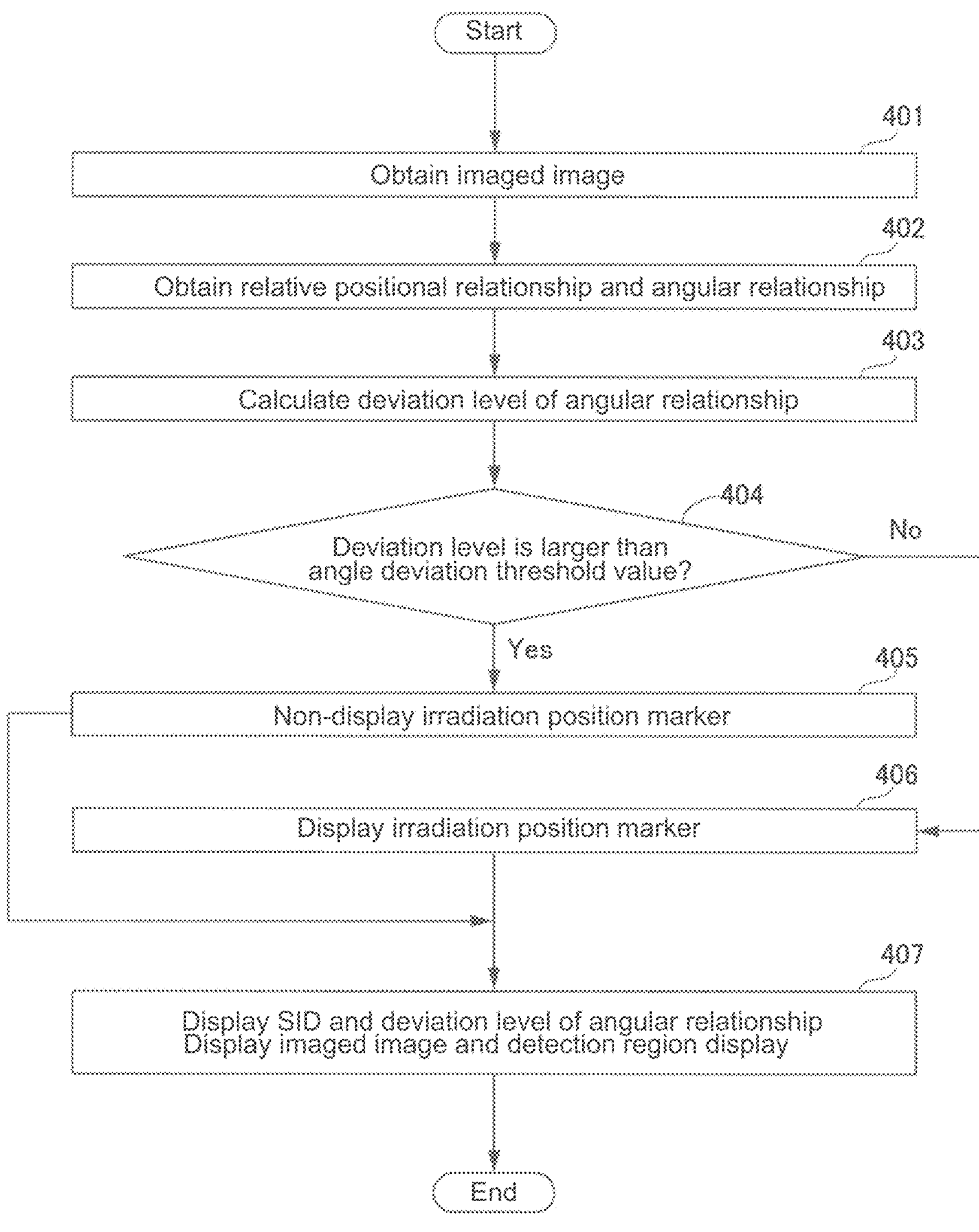
FIG. 8 is a flow chart illustrating a position determination supporting method according to the aspect of the Embodiment 1.

Next, referring to FIG. 8, the inventor sets forth a control processing of a supporting method of determining a position according to the aspect of the Embodiment 1. In addition, the control processing for the supporting method of determining the position is executed by the unit side control element 73 of the position determination support unit 7.

First, in Step 401, the marker member 71 installed to the X-ray detection element 2 arranged between the subject 101 and the bed 102 is imaged by the imaging element 72 to obtain the imaged image.

Nest, in Step 402, the marker member 71 is detected in the imaged image and accordingly, an arrangement of the X-ray detection element 2 relative to the X-ray irradiation element 1 is detected. Specifically, the relative positional relationship between the X-ray irradiation element 1 and the X-ray detection element 2 and the relative angular relationship between the detection surface 20 of the X-ray detection element 2 and the irradiation direction (W2-direction) of the X-ray from the X-ray irradiation element 1 are detected based on detecting the marker member 71 in the imaged image.

Next, in Step 403, the deviation level is calculated from the setting angle preliminarily set as to the detected angular relationship. Specifically, the roll angle deviation level that is the deviation level in the roll angle direction (φ-direction), wherein the longitudinal axis direction (X-direction) of the detection surface 20 of the X-ray detection element 2 is the rotation axis, and the pitch angle deviation level that is the deviation level in the pitch angle direction (φ-direction), wherein the horizontal axis direction (Y-direction) is the rotation axis, are calculated.

Next, in Step 404, it is decided whether the calculated deviation level is larger than the angle deviation threshold value or not. Specifically, it is decided whether the roll angle deviation level and the pitch angle deviation level are respectively larger than the angle deviation threshold value or not. When it is determined that the calculated deviation level is larger than the angle deviation threshold value, Step 405 proceeds. Further, when it is determined that the calculated deviation level is smaller than the angle deviation threshold value, Step 406 proceeds.

In Step 405, the irradiation position marker 90 is turned to the non-display. Specifically, when it is decided that the roll angle deviation level is larger than the angle deviation threshold value, the projection from the laser source 74 is turned off so that the display of the first projection light 91 becomes the non-display. Further, when it is decided that the pitch angle deviation level is larger than the angle deviation threshold value, the projection from the laser source 75 is turned off so that the display of the second projection light 92 becomes the non-display.

In Step 406, the irradiation position marker 90 is displayed. Specifically, when it is decided that the roll angle deviation level is smaller than the angle deviation threshold value, the projection from the laser source 74 is turned on so that the first projection light 91 is displayed. Further, when it is decided that the pitch angle deviation level is smaller than the angle deviation threshold value, the projection from the laser source 75 is turned on so that the second projection light 92 is displayed.

And in Step 407, the numeric value of the SID and the numeric values of the deviation level of the angular relationships (the roll angle deviation level and the pitch angle deviation level) are displayed on the display 8 based on the relative positional relationship and the relative angular relationship detected in Step 402. Further, the imaged image taken in Step 401 and the detection region display **8*a* denoting the region where detection the X-ray of the X-ray detection element 2 in the imaged image are superimposed and displayed on the display 8**.

In addition, the display of the specific numeric values of the roll angle deviation level and the pitch angle deviation level and the display of the imaged image and the detection region display **8*a* in Step 407 can be executed at any timing following Step 403. Further, the control processing in Steps 401-407 is executed repeatedly every time when one frame of the imaged image as the video image is obtained. In addition, the control processing in Step 401-Step 407** may be executed repeatedly every predetermined time interval regardless of the frame rate of the imaged image.

Experimental Result

Next, the inventor sets forth the experimental result obtained by carrying out to confirm the effect on the position determination support as to the X-ray imaging apparatus 100 (the position determination support unit 7) according to the aspect of the Embodiment 1.

According to the experiment, the X-ray imaging was carried out while adjusting the three-dimensional arrangement of the X-ray irradiation element 1 and also irradiating the X-ray toward the X-ray detection element 2 so that the imaging angle (the relative angle of the X-ray irradiation direction to the detection surface 20) becomes the predetermined numeric value. And the average time needed to carry out one X-ray imaging was obtained by carrying out the X-ray imaging multiple times while adjusting the arrangement of the X-ray irradiation element 1 every time. Further, when the angle deviation of the imaging angle was not within the predetermined range when carrying out the X-ray imaging, it was deemed as an imaging error and the X-ray imaging was redone. And the respective results when using the position determination support unit 7 according to the aspect of the Embodiment 1 and when not using according to the comparative Embodiment were compared.

The experimental result showed that the time needed for X-ray imaging using the position determination support unit 7 according to the Embodiment was approximately 26% less per one imaging than the comparative Embodiment. Further, whereas the event probability of the imaging error was approximately 40% in the comparative Embodiment, that was 0% in the aspect of the Embodiment 1. In addition, when the imaging error took place and the time needed for the X-ray imaging including the time needed to redo, the time needed for the X-ray imaging in the present Embodiment was approximately 51% shorter than in the comparative Embodiment.

Consequently, it was confirmed that the time needed for the X-ray imaging using the X-ray imaging apparatus 100 having the position determination support unit 7 according to the aspect of the Embodiment 1 could reduce the time needed for the X-ray imaging and lower the incidence rate of the imaging error. Therefore, an increase of the operation time can be suppressed, so that the burdens on the operator and the subject 100 can be alleviated. Further, the number of re-imaging can be reduced by decreasing the incidence rate of the imaging error, so that the increase of the radiation dosage for the subject 101 can be suppressed. Further, the adjustment as to the angular relationship is easy so that consistency of the generated X-ray image can be maintained and when the X-ray imaging for one subject 101 is carried out multiple times, the interpretation of the X-ray image can be accomplished easily.

Effect According to the Aspect of the Embodiment 1

The following effects can be obtained according to the aspect of the Embodiment 1.

According to the aspect of the Embodiment 1, the X-ray imaging apparatus 100 comprises the projection element **70*b* that projects the irradiation position marker 90 specifying the position to which the X-ray is irradiated from the X-ray irradiation element 1 on the body surface of the subject 101. And the projection element 70*b* is configured to change the display mode of the irradiation position marker 90 based on the deviation level corresponding to the preset angle of the angular relationship detected by the sensor element 70*a* (angular relationship detection element). Therefore, the irradiation position marker 90 is projected on the body surface of the subject 101 by the projection element 70*b*, so that the adjustment of the position where the X-ray is irradiated can be easily carried out by confirming the irradiation position marker 90. And the display mode of the projected irradiation position marker 90 is changed based on the deviation level of the angular relationship, so that whether the angular relationship is included in the adequate range or not can be intuitively recognized by visually confirming the irradiation position marker 90 differently from the case in which the projected numeric value is confirmed. Consequently, the adjustment of the relative angular relationship between the detection surface 20 of the X-ray detection element 2 and the irradiation direction of the X-ray from the X-ray irradiation element 1** is carried out easily in addition to adjusting the position where the X-ray is irradiated by intuitively recognizing the angular relationship.

Further, the adjustment of the relative angular relationship between the detection surface 20 of the X-ray detection element 2 and the irradiation direction of the X-ray from the X-ray irradiation element 1 in addition to adjusting the position where the X-ray is irradiated can be carried out easily by visually recognizing the irradiation position marker 90 projected on the body surface of the subject 101, so that the position determination of the X-ray irradiation element 1 can be carried out while confirming the condition of the subject 101. Therefore, it can be suppressed that the arrangement of the X-ray detection element 2 and the position determination of the X-ray irradiation element 1 must be redone due to shifting of the position of the subject 101 by that the subject 101 moves the body.

Further, according to the aspect of the Embodiment 1, the following configuration is adopted, so that the effects describe below can be obtained.

Specifically, according to the aspect of the Embodiment 1, as described above, the projection element **70*b* is configured to project the irradiation position marker 90 indicating the irradiation center of the X-ray irradiated from the X-ray irradiation element 1 on the body surface of the subject 101 and change the display mode of the irradiation position marker 90 indicating the position of the irradiation center. According to such a configuration, the irradiation position marker 90 indicating the irradiation center of the X-ray irradiated to the subject 101 is projected by the projection element 70*b*, so that the operator can recognize the center of the position where the X-ray is irradiated while confirming the subject 101. And the display mode of the projected irradiation position marker 90 indicating the irradiation center is changed based on the deviation level of the angular relationship, so that the operator can confirm whether the angular relationship is included in the adequate scope or not while recognizing more accurately the position of the irradiation center of the X-ray. Therefore, while confirming the subject 101 and recognizing accurately the position of the X-ray irradiated to the subject 101, the operator can adjust intuitively and easily the relative angular relationship between the detection surface 20 of the X-ray detection element 2 and the irradiation direction of the X-ray from the X-ray irradiation element 1** in addition to adjusting the position where the X-ray is irradiated.

Further, according to the aspect of the Embodiment 1, as set forth above, the projection element **70*b* is configured to change the display mode of the irradiation position marker 90 by switching at least two display modes selected from a group consisting of the display, the non-display and the blinking-display (blinking-display-mode) of the irradiation position marker 90 projected on the body surface of the subject 101 based on the deviation level relative to the setting angle of the angular relationship detected by the sensor element 70*a* (angular relationship detection element). According to such a configuration, the display mode of the irradiation position marker 90 is changed by switching the display and the non-display among the display, the non-display and the blinking-display of the irradiation position marker 90 based on the deviation level of the angular relationship, so that the operator can easily and visually recognize the deviation level of the angular relationship by recognizing the condition of the display and the non-display of the irradiation position marker 90. Therefore, it can be easily recognized whether the angular relationship is included in the adequate range or not by recognizing visually the irradiation position marker 90**, the adjustment of the angular relationship can be accomplished intuitively and easily.

Further, as set forth above according to the aspect of the Embodiment 1, the sensor element **70*a* (angular relationship detection element) is configured to detect the angular relationship relative to the roll angle direction (first rotation direction, φ-direction), wherein the rotation axis is the longitudinal axis direction of the longitudinal axis direction (X-direction) and the horizontal axis direction (Y-direction) orthogonal each other relative to the detection surface 20 of the X-ray detection element 2, and the angular relationship relative to the pitch angle direction (second rotation direction, θ-direction), wherein the horizontal axis direction is the rotation axis, and the projection element 70*b* is configured to change individually the display mode of the irradiation position marker 90 (first projection light 91) corresponding to the roll angle deviation level and the display mode of the irradiation position marker 90 (second projection light 92) corresponding to the pitch angle deviation level so that each of the roll angle deviation level (first deviation level) relative to the setting angle of the angular relationship in the roll angle direction and the pitch angle deviation level (second deviation level) relative to the setting angle of the angular relationship in the pitch angle direction becomes individually distinguishable. According to such a configuration, each of the roll angle deviation level in the roll angle direction and the pitch angle deviation level in the pitch angle direction can be individually distinguished by visually recognizing the irradiation position marker 90**, so that the operator can more easily recognize that the angular relationship must be adjusted to which direction between the roll angle direction and the pitch angle direction. Therefore, the operator can carry out further intuitively and easily the adjustment of the angular relationship.

Further, according to the aspect of the Embodiment 1, as described above, the projection element **70*b* is configured to project the cruciform irradiation position marker 90 indicating the position of the irradiation center of the X-ray irradiated from the X-ray irradiation element 1 by projecting the linear first projection light 91 and the linear second projection light 92 orthogonal each other on the body surface of the subject 101, and to change the display mode of the first projection light 91 which is either one of the first projection light 91 or the second projection light 92 based on the roll angle deviation level (first deviation level) and also to change the display mode of the second projection light 92 which is the other one of the first projection light 91 or the second projection light 92 based on the pitch angle deviation level (second deviation level). According to such a configuration, the irradiation position marker 90 has the cruciform indicating the position of the irradiation center, so that the position of the irradiation center can be more easily recognized by visually recognizing the cruciform intersection point. Further, the display mode of the first projection light 91 is changed based on the roll angle deviation level (first deviation level) and also the display mode of the first projection light 92 is changed based on the pitch angle deviation level (second deviation level), so that the adjustment of the angular relationship in the roll angle direction (first rotation direction, φ-direction) and the adjustment of the pitch angle direction (second rotation direction, θ-direction) can be accomplished individually and easily by recognizing each display mode of the linear first projection light 91 and the linear second projection light 92 forming the cruciform. Therefore, the adjustments of the respective angular relationships of the roll angle direction and the pitch angle direction can be easily accomplished by visually recognizing the irradiation position marker 90** having the cruciform, which is a simple shape.

Further, according to the aspect of the Embodiment 1, as set forth above, the projection element **70*b* is configured to turn the irradiation position marker 90 to the non-display when the deviation level relative to the setting angle of the angular relationship detected by the sensor element 70***a* (angular relationship detection element) is larger than the angle deviation threshold value which is preliminarily set, and to turn the irradiation position marker 90 to the display when the deviation level relative to the setting angle of the angular relationship is smaller than the angle deviation threshold value. According to such a configuration, the display and the non-display of the irradiation position marker 90 are switched in between, so that operator can more easily recognize whether the angular relationship is included in the adequate range or not. Therefore, in comparison with the case of carrying out more complicated change of the display mode, the adjustment of the angular relationship can be carried out more intuitively and easily.

Further, according to the aspect of the Embodiment 1, as described above, the setting angle is the orthogonal angle wherein the irradiation direction of the X-ray from the irradiation element 1 is orthogonal to the detection surface 20 of the X-ray detection element 2, and the projection element 70*b* is configured to change the display mode of the irradiation position marker 90 based on the deviation level relative to the orthogonal angle of the angular relationship detected by the sensor element 70*a* (angular relationship detection element). Here, the X-ray imaging is carried out relative to the orthogonal angle in which the irradiation direction of the X-ray is orthogonal to the detection surface 20, so that the visual recognition for the generated X-ray image can be improved in comparison with the case in which the irradiation direction is shifted from the orthogonal angle. Therefore, the display mode of the irradiation position marker 90 is changed based on the deviation level relative to the orthogonal angle of the angular relationship, so that the operator can easily recognize whether the angular relationship is the orthogonal angle or not. As a result. the operator can more easily adjust the angular relationship so that the visual recognition of the generated X-ray image increases.

Further, according to the aspect of the Embodiment 1, as described above, the sensor element 70*a* (angular relationship detection element) includes the marker member 71 installed to the X-ray detection element 2, the imaging element 72 that is arranged in the X-ray irradiation element 1 and images optically the marker member 71, and the unit side control element 73 (control element) that detects the angular relationship based on the marker member 71 imaged by the imaging element 72, and the unit side control element 73 is configured to calculate the deviation level relative to the setting angle of the angular relationship based on the detected angular relationship and change the display mode of the irradiation position marker 90 projected by the projection element 70*b* based on the deviation level relative to the setting angle of the calculated angular relationship. Here, when the electromagnetic wave emitted from the electromagnetic coil is detected by that the electromagnetic is in place coil to detect the relative positional relationship and angular relationship between the X-ray irradiation element 1 and the X-ray detection element 2, the detection precision may worsen due to the electromagnetic wave emitted from the electronic equipment arranged in the vicinity thereof. Whereas, according to the aspect of the Embodiment 1, the position detection is carried out by optically imaging the marker member 71 installed to the X-ray detection element 2, so that it can be suppressed that the detection precision worsens due to the electromagnetic wave emitted from the electronic equipment arranged in the vicinity thereof.

Further, according to the aspect of the Embodiment 1, as described above, the projection element 70*b*, the imaging element 72 and the unit side control element 73 are demountable as to the X-ray irradiation element 1. In such a configuration, the projection element 70*b*, the imaging element 72 and the unit side control element 73 are demountable as to the irradiation element 1, so that the position determination support unit 7 (projection element 70*b*, imaging element 72 and unit side control element 73) can be mounted later on the existing X-ray imaging apparatus. Therefore, when using the existing X-ray imaging apparatus, the position determination support unit 7 (projection element 70*b*, imaging element 72 and unit side control element 73) is equipped therewith, the adjustment of the relative angular relationship between the detection surface 20 and the irradiation direction of the X-ray from the X 2-ray irradiation element 1 is carried out easily and intuitively in addition to adjusting the position where the X-ray is irradiated while confirming the subject 101.

Embodiment 2

Figure 9:
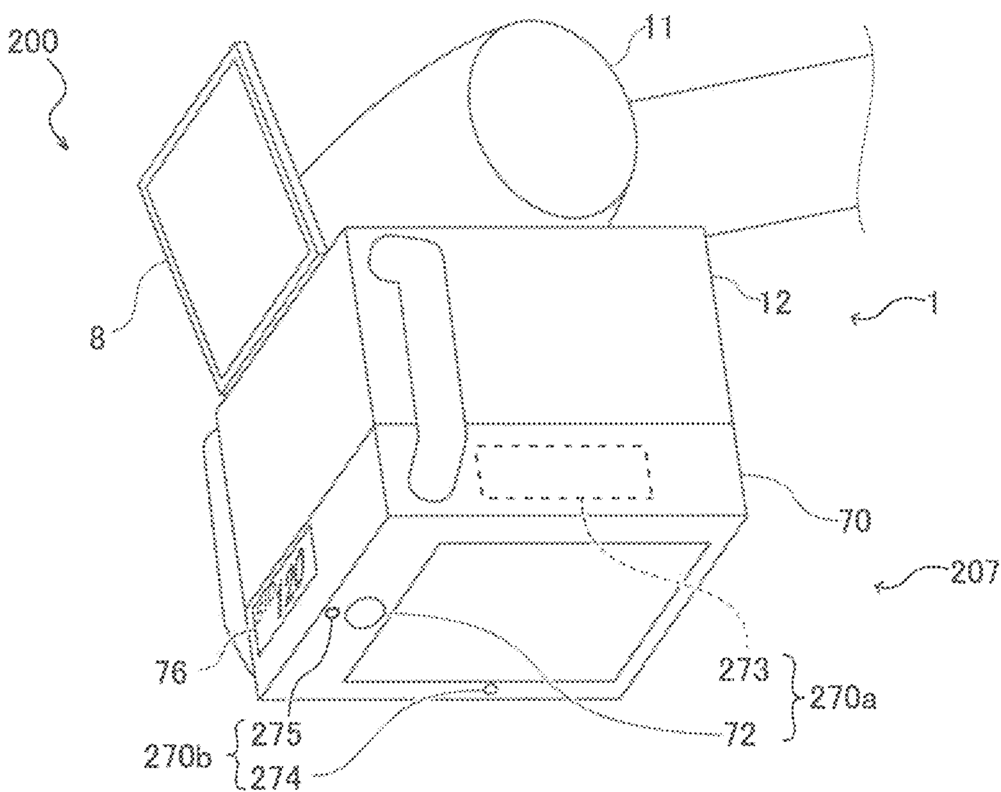
FIG. 9 is a schematic view illustrating the position determination support unit for the X-ray imaging apparatus according to the aspect of the Embodiment 2.
Figure 10:
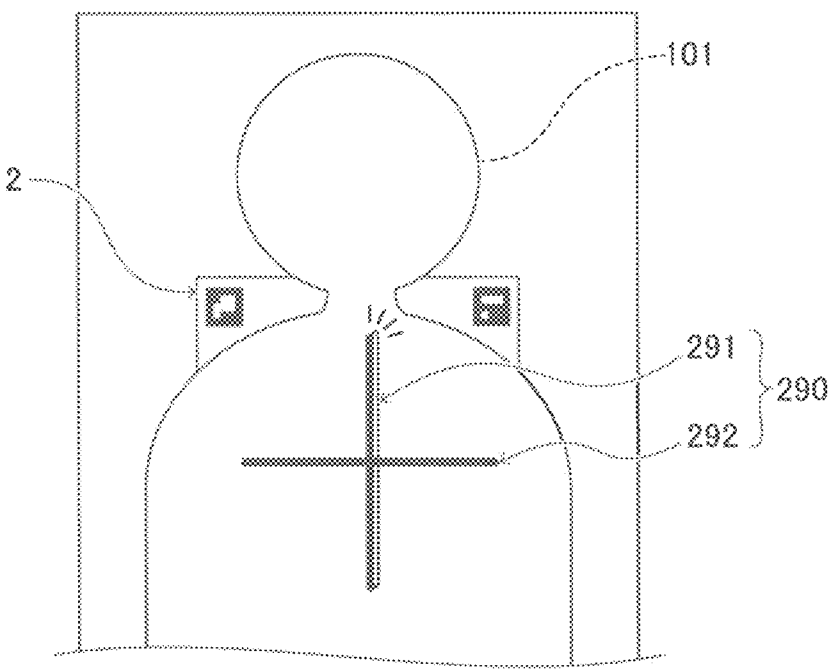
FIG. 10 is a schematic view illustrating change of the display mode of the irradiation position marker according to the aspect of the Embodiment 2.

Referring to FIG. 9, FIG. 10, the inventor sets forth a configuration of the X-ray imaging apparatus 200 according to the aspect of the Embodiment 2. According to the aspect of the Embodiment 2, when the deviation level is large, an irradiation position marker 290 is blinked and also the blinking cycle of the irradiation position marker 290 is changed corresponding to the deviation level, differently from the Embodiment 1 wherein the display mode of the irradiation position marker 90 is switched between the display and the non-display based on the deviation level relative to the setting angle of the angular relationship. In addition, in FIG., the same component as the Embodiment 1 described above is provided with the same sign to be shown and also the explanation thereof is skipped.

Configuration of an X-Ray Imaging Apparatus According to the Aspect of the Embodiment 2

Referring to FIG. 9, FIG. 10, the X-ray imaging apparatus 200 according to the aspect of the Embodiment 2 comprises a position determination support unit 207. The position determination support unit 207 includes the sensor element 270*a* and the projection element 270*b*. The sensor element 270*a* includes the unit side control element 273. The hardware configuration of the unit side control element 273 is the same as the unit side control element 73 according to the Embodiment 1. Further, the projection element 270*b* includes a laser source 274 and a laser source 275. The configurations of the laser source 274 and the laser source 275 are the same as the laser source 74 and the laser source 75 according to the aspect of the Embodiment 1 and the projection element 70*b* and the laser source 275 are configured to project the cruciform irradiation position marker 290 by respectively projecting the linear first projection light 291 and the linear second projection light 292. In addition, the sensor element 270*a* is an example of an "angular relationship detection element" and a "positional relationship detection element" in Claims. Further, the unit side control element 273 is an example of a "control element" in Claims.

Referring to FIG. 10, according to the aspect of the Embodiment 2, the projection element 270*b* is configured to turn the irradiation position marker 290 to the blinking-display when the deviation level relative to the setting angle of the angular relationship detected by the sensor element 270*a* is larger than the preset angle deviation threshold value. And the projection element 270*b* is configured to change the blinking cycle of the blinking-display of the irradiation position marker 290 corresponding to the deviation level relative to the setting angle of the angular relationship.

Specifically, the unit side control element 273 calculates respectively the roll angle deviation level and the pitch angle deviation level as well as the unit side control element 73 according to the aspect of the Embodiment 1. And the unit side control element 273 changes the display mode of the first projection light 291 from the laser source 274 of the projection element 270*b* based on the roll angle deviation level. Further, the unit side control element 273 changes the display mode of the second projection light 292 from the laser source 275 of the projection element 270*b* individually from the first projection light 291 based on the pitch angle deviation level.

In detail, the unit side control element 273 displays the first projection light 291 by turning on the laser source 274 when the roll angle deviation level is smaller than the preset angle deviation threshold value. Also, the unit side control element 273 displays the first projection light 291 by turning on the laser source 274 when the roll angle deviation level is smaller than the preset angle deviation threshold value.

And, according to the aspect of the Embodiment 2, the unit side control element 273 displays the first projection light 291 with blinking when the roll angle deviation level is larger than the angle deviation threshold value. Further, the unit side control element 273 displays the second projection light 292 with blinking when the pitch angle deviation level is larger than angle deviation threshold value. And the unit side control element 273 makes the larger deviation level, the larger blinking cycle of the blinking-display corresponding to the level of each deviation level relative to the setting angle of the angular relationship (the roll angle deviation level and the pitch angle deviation level).

For example, the length of the blinking cycle is set as every 0.5 seconds given the angle deviation threshold value is 4 degree and given the angular relationship deviation level is larger than 4 degree and smaller than 10 degrees. Further, the blinking cycle is set as every 1 second given the deviation level is larger than the 10 degrees. In addition, the change of the blinking cycle may be more than 2 phases. Further, the blinking cycle can be linearly changed along the increase of the deviation level of the angular relationship.

In addition, referring to FIG. 10, each example when the roll angle deviation level is smaller than the angle deviation threshold value and when the pitch angle deviation level is larger than the angle deviation threshold value is shown. In such a case, the first projection light 291 is displayed (constantly light-on) and the second projection light 292 is displayed as blinking. Further, the other configuration according to the aspect of the Embodiment 2 is the same as the aspect of the Embodiment 1 above described.

Effect According to the Aspect of the Embodiment 2

The following effect can be obtained according to the aspect of the Embodiment 2.

According to the aspect of the Embodiment 2, as set forth above, the projection element 270*b* is configured to turn the irradiation position marker 290 to the blinking-display when the deviation level relative to the setting angle of the angular relationship detected by the sensor element 270*a* (angular relationship detection element) is larger than the angle deviation threshold value which is preliminarily set, and to change the blinking cycle at the blinking-display of the irradiation position marker 290 corresponding to the deviation level relative to the setting angle of the angular relationship. In such a configuration, the blinking cycle of the blinking-display is changed corresponding to the deviation level, so that the difference between the scales of the deviation level of the angular relationship can be easily and visually recognized by visually recognizing the irradiation marker 290. Therefore, what level of the adjustment of the angular relationship is needed can be recognized intuitively by recognizing the blinking cycle of the irradiation position marker 290.

In addition, the other effect according to the aspect of the Embodiment 2 is the same as the aspect of the Embodiment 1 described above.

Embodiment 3

Figure 11:
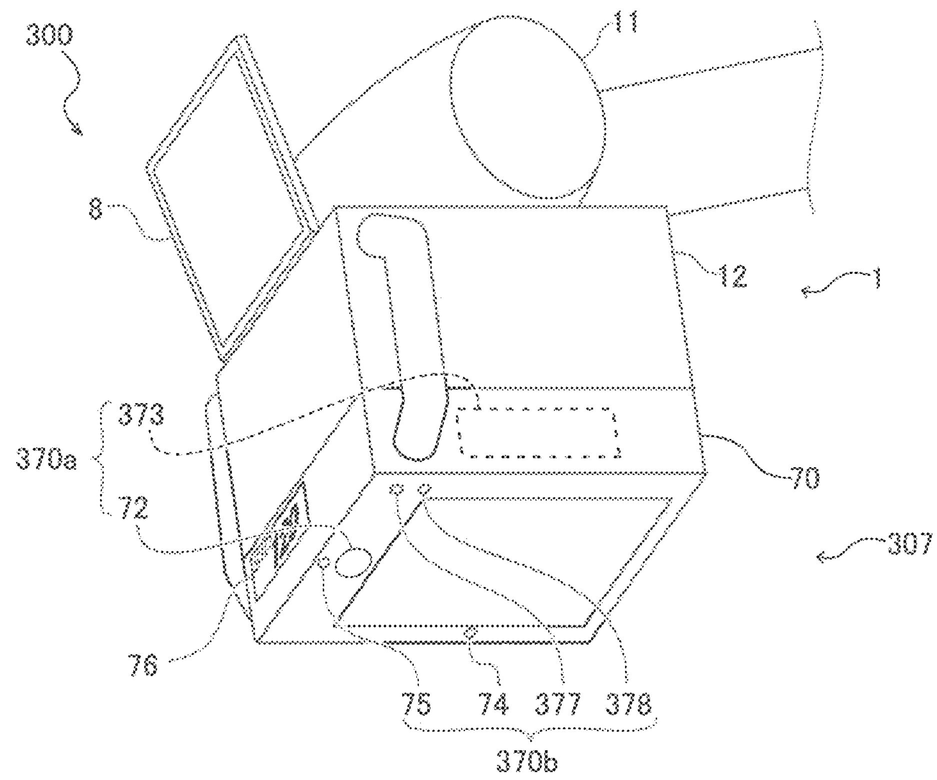
FIG. 11 is a schematic view illustrating the position determination support unit for the X-ray imaging apparatus according to the aspect of the Embodiment 3.
Figure 12:
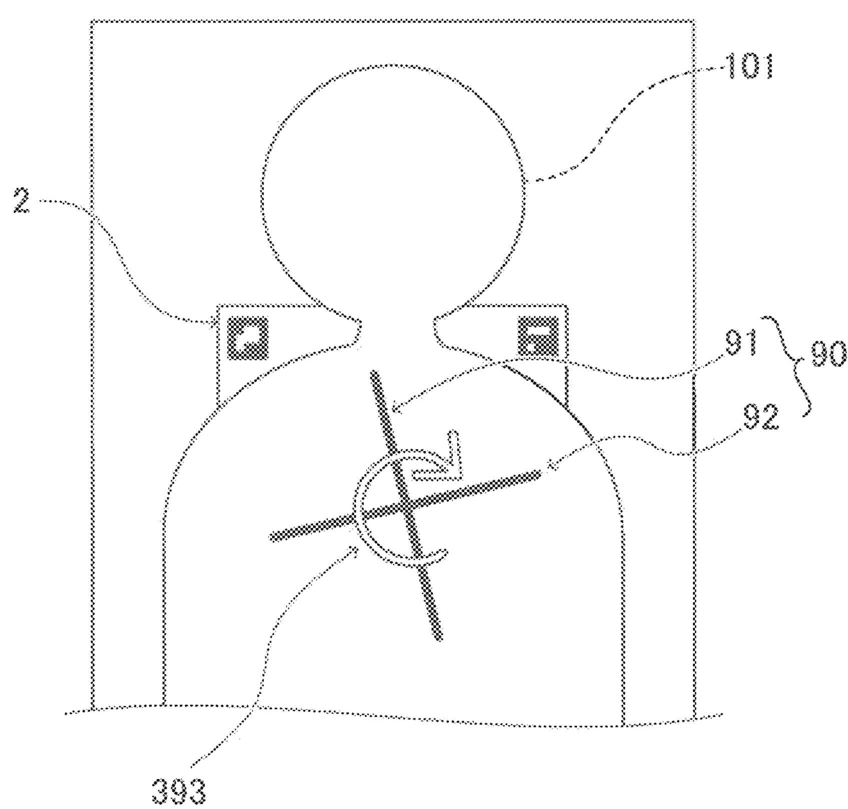
FIG. 12 is a schematic view illustrating the display mode of a rotation direction marker according to the aspect of the Embodiment 3.
Figure 13:
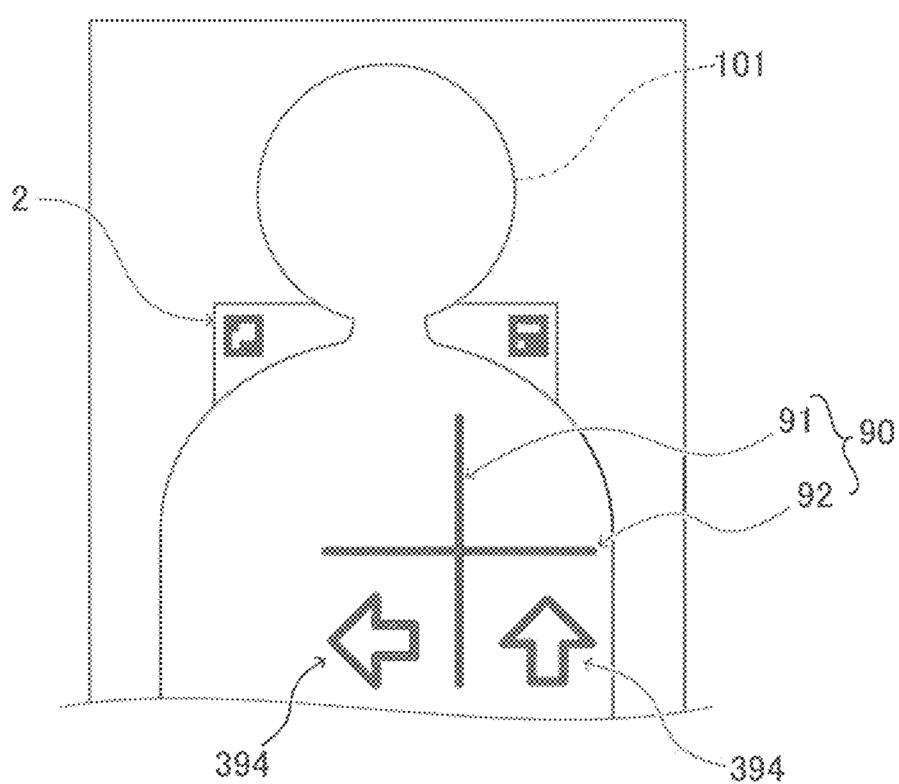
FIG. 13 is a schematic view illustrating the display mode of a moving direction marker according to the aspect of the Embodiment 3.

Referring to FIG. 11 to FIG. 13, the inventor sets forth the configuration of the X-ray imaging apparatus 300 according to the aspect of the Embodiment 3. According to the aspect of the Embodiment 3, a rotation instruction marker 393 and a moving instruction marker 394 are projected in addition to the irradiation position marker 90. In addition, the same component as described in the Embodiment 1 and the Embodiment 2 is provided with the same sign to be shown and also the explanation thereof is skipped.

Configuration of an X-Ray Imaging Apparatus According to the Aspect of the Embodiment 3

Referring to FIG. 11, the aspect of the Embodiment 3, the X-ray imaging apparatus 300 comprises a position determination support unit 307. The position determination support unit 307 includes a sensor element 370*a* and a projection element 370*b*. The sensor element 370*a* includes a unit side control element 373. The hardware configuration of the unit side control element 373 is the same as the unit side control element 73 according to the aspect of the Embodiment 1. In addition, the sensor element 370*a* is an example of an "angular relationship detection element" and a "positional relationship detection element" in Claims. Further, the unit side control element 373 is an example of a "control element" in Claims.

According to the aspect of the Embodiment 3, the projection element 370*b* includes both a laser source 377 and a laser source 378 that project the irradiation position marker 90 (the first projection light 91 and the second projection light 92) in addition to the laser source 74 and the laser source 75. The laser source 377 and the laser source 378 are the laser projectors that project a figure on the body surface of the subject 101 by projecting the laser light. The laser source 377 and the laser source 378 as well as the laser source 74 and the laser source 75 are in place in the X-ray irradiation side in the unit housing element 70 of the position determination support unit 307.

And the unit side control element 373 projects the irradiation position marker 90 on the body surface of the subject 101 as well as the aspect of the Embodiment 1 by controlling the operation of the laser source 74 and laser source 75 of the projection element 370*b*. Further, as well as the aspect of the Embodiment 1, the unit side control element 373 is configured to change the display mode by switching the display of the irradiation position marker 90 between the display and the non-display based on the deviation level of the detected angular relationship.

And referring to FIG. 12 and FIG. 13, according to the aspect of the Embodiment 3, the projection element 370*b* is configured to project the rotation instruction marker 393 and the moving instruction marker 394 in addition to the irradiation position marker 90 on the body surface of the subject 101 by the control that the unit side control element 373 executes.

Referring to FIG. 12, according to the aspect of the Embodiment 3, the laser source 377 of the projection element 270*b* is configured to project the irradiation position marker 393 on the body surface of the subject 101 by the control the unit side control element 373 executes. The rotation instruction marker 393 is the display instructing the change of the angular relationship along the yaw angle direction (the third rotation direction, ψ-direction). And the laser source 377 of the projection element 270*b* is configured to change the display mode of the rotation instruction marker 393 based on the deviation level corresponding to the preset angle of the angular relationship.

Specifically, as well as the aspect of the Embodiment 1, the unit side control element 373 detects the relative angle relationship between the irradiation direction (W2-direction) of the X-ray of the X-ray irradiation element 1 and the detection surface 20 of the X-ray detection element 2 as to the yaw angle direction (ψ-direction). And, according to the aspect of the Embodiment 3, the unit side control element 373 calculates the yaw angle deviation level that is the deviation level relative to the setting angle of the angular relationship in the yaw angle direction (ψ-direction) of the X-ray detection element 2 as well as roll angle deviation level and the pitch angle deviation level.

And the unit side control element 373 changes the display mode by switching the display mode of the rotation instruction marker 393 between the display and the non-display based on the calculated yaw angle deviation level. Specifically, the unit side control element 373 displays the rotation instruction marker 393 when the calculated yaw angle deviation level is larger than the preset angle deviation threshold value and suspends the display of the rotation instruction marker 393 when the calculated yaw angle deviation level is smaller than the angle deviation threshold value. The rotation instruction marker 393 is the figure denoting the direction along the yaw angle direction (ψ-direction) to make the yaw angle deviation level small. For example, the rotation instruction marker 393 is the curved arrow along a circle.

Further, referring to FIG. 13, according to the aspect of the Embodiment 3, the laser source 378 of the projection element 70*b* is configured to irradiate the moving instruction marker 394 on the body surface of the subject 101 by the control the unit side control element 373 executes. The moving instruction marker 394 instructs displaying the change of the positional relationship in the direction along the detection surface 20 of the X-ray detection element 2. And the laser source 378 of the projection element 370*b* is configured to change the display mode for the moving instruction marker 394 based on the deviation level corresponding to the preset angle of the positional relationship detected by the unit side control element 373 of the sensor element 370*a* (positional relationship detection element).

Specifically, as well as the aspect of the Embodiment 1, the unit side control element 373 detects the relative positional relationship between the X-ray irradiation element 1 and the X-ray detection element 2 for the X-ray tube 1 in the respective triaxial direction of the longitudinal axis direction (X-direction) of the detection surface 20, the horizontal axis direction (Y-direction), and the orthogonal direction (Z-direction) orthogonal to the detection surface 20. And, according to the aspect of the Embodiment 3, the unit side control element 373 calculates the deviation level from the setting position preliminarily set relative to the respective relative positional relationship as to the direction of the longitudinal axis (X-direction) and the direction of the horizontal axis (Y-direction) of the detection surface 20 of the X-ray detection element 2. The setting position preliminarily set is a position making the positional relationship wherein the center position of the irradiation center of the X-ray overlaps the center position of the detection surface 20.

And the unit side control element 373 changes the display mode by switching the moving instruction marker 394 between the display and the non-display based on the deviation level of the detected positional relationship. Specifically, the unit side control element 373 displays the moving instruction marker 394 when the deviation level of the calculated relative position is larger than the preset deviation threshold value and suspends the display of the moving instruction marker 394 when the deviation level of the calculated relative position is smaller than the preset deviation threshold value. For example, the moving instruction marker 394 includes an arrow indicating the direction along the X-direction to instruct the moving in the direction along the X-direction and an arrow indicating the direction along the Y-direction to instruct the moving in the direction along the Y-direction. The unit side control element 273 individually changes the display mode between the display mode of the moving instruction marker 394 that instructs moving in the direction along the X-direction and the display mode of the moving instruction marker 394 that instructs moving in the direction along the Y-direction based on the deviation level of the relative position in the respective longitudinal axis direction (X-direction) and the horizontal axis direction (Y-direction). Further, the positional deviation threshold value preliminarily set is stored in the memory device of the unit side control element 373 as well as the angle deviation threshold value.

Further, in other configuration elements according to the aspect of the Embodiment 3 is the same as the aspect of the Embodiment 1 as Embodiment 1 and set forth above.

Effect According to the Aspect of the Embodiment 3

The following effect can be obtained according to the aspect of the Embodiment 3.

According to the aspect of the Embodiment 3, as set forth above, the sensor element 370*a* (angular relationship detection element) is configured to detect the angular relationship in the yaw angle direction (the third rotation direction, ψ=direction) in which the rotation direction is the orthogonal direction to the detection surface 20 of the X-ray detection element 2, the projection element 370*b* is configured to project the rotation instruction marker 393, which instructs the change of the angular relationship along the yaw angle direction, on the body surface of the subject 101, and wherein the display mode of the rotation instruction marker 393 is changed based on the deviation level corresponding to the setting angle of the angular relationship. Here, when the angular relationship is deviated in the yaw direction, the region of the irradiation field is deviated is in the cocked state relative to the detection surface 20 of the X-ray detection element 2. In such a case, the portion where the X-ray is not irradiated in the region of the detection surface 20 emerges, so that a part of the generated X-ray image becomes lost. In contrast, according to the aspect of the Embodiment 3, the projection element 370*b* is configured to project the rotation instruction marker 393, which instructs the change of the angular relationship along the yaw angle direction, on the body surface of the subject 101, wherein the display mode of the rotation instruction marker 393 is changed based on the deviation level corresponding to the setting angle of the angular relationship, so that the angular relationship of the yaw angle direction can be easily adjusted by recognizing the display mode of the rotation instruction marker 393. As a result, it is easily recognized that a part of the general X-ray image becomes lost.

Specifically, according to the aspect of the Embodiment 3, as described above, the sensor element 370*a* (positional relationship detection element) that detects the relative positional relationship between the detection surface 20 and the X-ray irradiation element 1 is included, the projection element 370*b* is configured to project the moving instruction marker 394 instructing the change of the positional relationship in the direction along the detection surface 20 of the X-ray detection element 2 on the body surface of the subject 101, and configured to change the display mode of the irradiation position marker 394 based on the deviation level relative to the preset setting position of the positional relationship detected by the sensor element 370*a*. According to such a configuration, the deviation level of the positional relationship in addition to the deviation level of the angular relationship can be easily recognized by recognizing the moving instruction marker 394, so that the adjustment of the positional relationship in addition to the angular relationship can be easily accomplished.

In addition, other effects according to the aspect of the Embodiment 3 are the same as the aspect of the Embodiment 1 and the Embodiment 2.

Alternative Embodiment

In addition, the aspects of the Embodiments and the Embodiments disclosed at this time are examples and not limited thereto in any points. The scope of the present invention is specified in the claims but not in the above description of the aspect of the Embodiments and all alternative (alternative Embodiments) are included in the scope of the claims and equivalents thereof.

For example, according to the aspect of the Embodiments 1 to 3 described above, the configuration example of that the X-ray irradiation position marker 90 (290) projected by the projection element 70*b* (270*b*, 370*b*) denotes the position of the irradiation center of the X-ray, but the present invention is not limited thereto. According to the present invention, the irradiation position marker projected by the projection element can be the display denoting the shape of the irradiation field of the X-ray irradiated from the X-ray irradiation element.

Further, according to the aspect of the Embodiments 1 to 3, as set forth above, the example is illustrated that the display mode of the irradiation position marker 90 (290) is changed by switching at least two display modes selected from a group consisting of the display, the non-display and the blinking-display of the irradiation position marker 90 (290) based on the deviation level of the angular relationship, but the present invention is not limited thereto. According to the present invention, the display mode can be changed by changing the color of the irradiation position marker based on the deviation level of the angular relationship angular. Further, the display mode can be changed by changing the shape (type) of the irradiation position marker based on the deviation level of the angular relationship angular.

Further, according to the aspect of the Embodiment 1, the configuration examples are illustrated as when the deviation level of the angular relationship is larger than the angle deviation threshold value, an irradiation position marker 90 is turned to the non-display; also when smaller than the angle deviation threshold value, the irradiation position marker 90 is turned to the display; and according to the aspect of the Embodiment 2, when the deviation level of the angular relationship is larger than the angle deviation threshold value, the irradiation position marker 90 is turned to the blinking-display; and also the blinking cycle of the blinking-display of the irradiation position marker 290 is changed corresponding to the deviation level of the angular relationship, but the present invention is not limited thereto. According to the present invention, when smaller than the angle deviation threshold value, the irradiation position marker is displayed and when the deviation level of the angular relationship is larger than the angle deviation threshold value, the irradiation position marker may be subject to blink in a constant cycle. Further, when smaller than the angle deviation threshold value, the irradiation position marker becomes the blinking-display, and also when the deviation level of the angular relationship is larger than the angle deviation threshold value, the irradiation position marker cannot be blinked, but can become the display without blinking (constant light-on).

Further, according to the aspect of the Embodiments 2, as set forth above, the example in which the blinking cycle becomes large corresponding to the deviation level of the angular relationship, but the present invention is not limited thereto. According to the aspect of the present invention, the blinking cycle can be shorter corresponding to the deviation level of the angular relationship.

Further, according to the aspect of the Embodiment 3, the examples are shown, wherein the display mode is changed to switching between the display and the non-display of the rotation instruction marker 393 based on the yaw angle deviation level that is the deviation level of the angular relationship in the yaw angle direction (third rotation direction) and the display mode is changed to switching between the display and the non-display of the moving instruction marker 394 based on the deviation level of the positional relationship, but the present invention is not limited thereto. According to the present invention, changes of the display mode of the rotation instruction marker and the moving instruction marker can be accomplished by switching between the display and the non-display as well as the aspect of the Embodiment 2. In such a case, the blinking cycle can be changed corresponding to the deviation level as well as the aspect of the Embodiment 2.

Further, according to the aspect of the Embodiment 1 to 3 as described above, the example is illustrated wherein the angular relationship is adjusted in the rotation direction in which the longitudinal axis direction and the horizontal axis direction orthogonal to each other on the detection surface 20 of the X-ray detection element 2 are respectively the rotation axes, but the present invention is not limited thereto. According to the present invention, the angular relationship can be adjusted in the rotation direction of the rotation axis in the crocked direction from the longitudinal axis and the horizontal axis of the detection surface.

Further, according to the aspect of the Embodiment 1 to 3 as described above, the example is illustrated wherein the cruciform is formed of the first projection light 91 (291) and the second projection light 92 (292) when the irradiation position marker 90 (290) are projected linearly, but the present invention is not limited thereto. According to the present invention, the irradiation position marker may denote the irradiation center of the X-ray by projecting one point like projection light. Further, the irradiation position marker can denote the irradiation center of the X-ray by projecting multiple projection lights more than three.

Further, according to the Embodiment 1 to 3, the examples illustrate wherein the display mode of the first projection light 91 projected as extending along the axis (U-direction) corresponding to the longitudinal axis direction (X-direction) that is the rotation axis in the roll angle direction (first rotation direction) is changed based on the roll angle deviation level (first deviation level), and the display mode of the second projection light 92 projected as extending along the axis (V-direction) corresponding to the horizontal axis direction (Y-direction) that is the rotation axis in the pitch angle direction (second rotation direction) is changed based on the pitch angle deviation level (second deviation level), but the present invention is not limited thereto. According to the present invention, the display mode of the second projection light can be changed based on the first deviation level, and the display mode of the first projection light can be changed based on the second deviation level.

Further, according to the aspect of the Embodiment 1 to 3, the example illustrates that the setting angle preliminarily set to calculate the angle deviation is the orthogonal angle that is the angular relationship in which the irradiation direction of the X-ray of the X-ray irradiation element 1 is orthogonal to the detection surface 20 of the X-ray detection element 2, but the present invention is not limited thereto. According to the present invention, the setting angle can be set as the angle crocked from the angular relationship in which the irradiation direction is orthogonal to the detection surface of the irradiation detection element.

Further, according to the aspect of the Embodiment 1 to 3, the example illustrates that the relative position (position and angle) of the X-ray detection element 2 to the X-ray irradiation element 1 is detected by that the imaging element 72 images the marker member 71 installed to the X-ray detection element 2, but the present invention is not limited thereto. According to the present Embodiment, the arrangement of the X-ray detection element can be detected by executing the control processing for the image recognition from the imaged image that imaged x-ray detection element without placing the marker member 71. Further, the relative angular relationship between the irradiation direction of the X-ray of the X-ray and the X-ray detection element irradiation element can be detected by detecting an infrared light, a radio wave (electromagnetic wave) or a ultrasound wave. Further, the relative angle relationship can be detected by arranging the angle sensor respectively to the X-ray irradiation element and the X-ray detection element.

Further, according to the Embodiment 1 to 3, the example illustrates the configuration in which the projection element **70*b* (270*b*, 370*b*) of the position determination support unit 7, 07, 307 (position determination unit for the X-ray imaging apparatus), the imaging element 72, and the unit side control element 73, 273, 373** (control element) are installed to be demountable (mountable later), but the present invention is not limited thereto. According to the present Embodiment, the projection element, the imaging element, and the control element can be formed with the X-ray irradiation element in a unified manner.

Further, according to the aspect of the Embodiments 1, 2 describe above, the examples illustrate that the irradiation position marker 90 (290) is projected and according to the aspect of the Embodiment 3, the rotation instruction marker 393 and the moving instruction marker 394 are projected in addition to the irradiation position marker 90, but the present invention is not limited thereto. According to the present invention, the deviation level of the angular relationship, the deviation level of the positional relationship and the specific numeric value indicating the SID can be projected in addition to the irradiation position marker 90. In such a case, the numeric value can be projected on the shifted position from the body surface of the subject.

Further, according to the aspect of the Embodiments 1 to 3 set forth above, the examples illustrate that the projection element **70*b* (270*b*, 370*b*) consists of the laser source 74 (75, 274, 275, 377, 378**), but the present invention is not limited thereto. According to the present invention, the projection element may consist of the projector that projects the image drawn on the liquid crystal display. Further, the projection element may consist of the LED (luminescence diode) that project light rather than laser light.

Further, according to the aspect of the Embodiments 1 to 3 set forth above, the example illustrates that the separate hardware consists of the unit side control element 73 (273, 373) that executes the control processing for the position determination support method and the main body side control element 3 that executes the control processing for the X-ray imaging, but the present invention is not limited thereto. According to the present invention, one common control element (hardware) can execute both the control processing for the position determination support method and the control processing for the X-ray imaging. For example, the main body side control element that control the X-ray imaging may execute the processing for detecting the relative angular relationship between the detection surface of the X-ray detection element and the irradiation direction of the X-ray of the X-ray irradiation element and the processing for projecting the irradiation position marker on the body surface of the subject.

Aspect

The above described, e.g., Embodiments can be understood as the below specific Embodiments by a person skilled in the art.

Term 1

An X-ray imaging apparatus comprises: an X-ray irradiation element that irradiates an X-ray to a subject; an X-ray detection element that detects an X-ray irradiated from the X-ray irradiation element; an angular relationship detection unit that detects a relative angular relationship between a detection surface of the X-ray detection element and an irradiation direction of the X-ray of the X-ray irradiation element; and a projection element that projects an irradiation position marker specifying a position where the X-ray is irradiated from the X-ray irradiation element on a body surface of the subject, wherein the projection element is configured to change a display mode for the irradiation position marker based on a deviation level corresponding to a preset angle of the angular relationship detected by the angular relationship detection element.

Term 2

The X-ray imaging apparatus according to Term 1, wherein the projection element is configured to project the irradiation position marker indicating the irradiation center of the X-ray irradiated from the X-ray irradiation element on the body surface of the subject, and change the display mode of the irradiation position marker indicating the position of the irradiation center based on the deviation level relative to the setting angle of said angular relationship.

Term 3

The X-ray imaging apparatus according to Term 1 or Term 2, the projection element is configured to change the display mode of the irradiation position marker by switching at least two of the display, the non-display and the blinking-display of the irradiation position marker projected on the body surface of the subject based on the deviation level relative to the setting angle of the angular relationship detected by the angular relationship detection element.

Term 4

The X-ray imaging apparatus according to Term 3, wherein the angular relationship detection element is configured to detect the angular relationship between a first rotation direction, of which a longitudinal axis direction is a rotation axis, and a second rotation direction, of which a rotation axis is a horizontal axis direction, between the longitudinal axis direction and the horizontal axis direction are orthogonal each other on the detection surface of the X-ray detection element, and the projection element is configured to change individually the display mode of the irradiation position marker corresponding to the first deviation level and the display mode of the irradiation position marker corresponding to the second deviation level so that each of the first deviation level relative to the setting angle of the angular relationship in the first rotation direction and the second deviation level relative to the setting angle of the angular relationship in the second rotation direction and the pitch angle deviation level becomes individually distinguishable.

Term 5

The X-ray imaging apparatus according to Term 4, wherein the projection element is configured to project the cruciform irradiation position marker indicating the position of the irradiation center of the X-ray irradiated from the X-ray irradiation element by projecting the linear first projection light and the linear second projection light orthogonal each other on the body surface of the subject, to change the display mode of either one of the first projection light or the second projection light based on the first deviation level, and in addition to change the display mode of the other one of the first projection light and the second projection light based on the second deviation level.

Term 6

The X-ray imaging apparatus according to any one of Term 3 to Term 5, wherein the projection element is configured to turn the irradiation position marker to the non-display when the deviation level relative to the setting angle of the angular relationship detected by the angular relationship detection element is larger than the angle deviation threshold value preliminarily set, and to turn the irradiation position marker to the display when the deviation level relative to the setting angle of the angular relationship is smaller than the angle deviation threshold value.

Term 7

The X-ray imaging apparatus according to any one of Term 3 to Term 5, the projection element is configured to turn the irradiation position marker to the blinking-display when the deviation level relative to the setting angle of the angular relationship detected by the angular relationship detection element is larger than the angle deviation threshold value preliminarily set, and to change a blinking cycle of in the blinking-display of the irradiation position marker corresponding to the deviation level relative to the setting angle of the angular relationship.

Term 8

The X-ray imaging apparatus according to any one of Term 1 to Term 7, wherein the setting angle is an orthogonal angle that is the angular relationship in which the irradiation direction of the X-ray of the X-ray irradiation element is orthogonal to the detection surface of the X-ray detection element, and the projection element changes the display mode for the irradiation position marker based on the deviation level relative to the orthogonal angle of the angular relationship detected by the angular relationship detection element.

Term 9

The X-ray imaging apparatus according to any one of Term 1 to Term 8, wherein the angular relationship detection element is configured to detect the angular relationship in the third rotation direction wherein the orthogonal direction orthogonal to the detection surface of the detection element is the rotation axis, and the projection element is configured to project the rotation instruction marker on the body surface of the subject to instruct the change of the angular relationship along the third rotation direction and change the display mode of the rotation instruction marker based on the deviation level relative to the setting angle of the angular relationship.

Term 10

The X-ray imaging apparatus according to any one of Term 1 to Term 9, wherein the angular relationship detection element further comprises: a marker member installed to the X-ray detection element; an imaging element that is arranged in the X-ray irradiation element and images optically the image marker member; and the control element that detects the angular relationship based on the marker member imaged by the imaging element, wherein the control element is configured to calculate the deviation level relative to the setting angle of the angular relationship based on the detected angular relationship, and to change the display mode of the irradiation position marker projected by the projection element based on the deviation level relative to the setting angle of the calculated angular relationship.

Term 11

The X-ray imaging apparatus according to Term 10, wherein the projection element, the imaging element, and the control element are demountable on the X-ray irradiation element.

Term 12

The X-ray imaging apparatus according to any one of Term 1 to Term 11, further comprises: a position detection element that detects a relative positional relationship between the X-ray detection element and the X-ray irradiation element, wherein the projection element is configured to project the moving instruction marker to instruct a change of the positional relationship in the direction along the detection surface of the X-ray detection element on the body surface of the subject, and to change the display mode of the moving instruction marker based on the deviation level relative to the preset setting position of the positional relationship detected by the positional relationship detection element.

Term 13

A position determination support unit for the X-ray imaging apparatus, comprises: the angular relationship detection element that detects relative angular relationship between an irradiation direction of the X-ray of the X-ray irradiation element that irradiates the X-ray and the detection surface of the X-ray detection element that detects the X-ray irradiated from the X-ray irradiation element; and the projection element that projects an irradiation position marker specifying the position where the X-ray is irradiated from the X-ray irradiation element on the body surface of the subject, wherein the projection element is configured to change the display mode for the irradiation position marker based on the deviation level relative to the preset angle of the angular relationship detected by the angular relationship detection element.

REFERENCE LIST

1 X-ray irradiation element
2 X-ray detection element
7, 207, 307 Position determination support unit (Position determination support unit for X-ray imaging apparatus) Detection surface
70*a*, 270*a*, 370*a* Sensor element (Angular relationship detection element, Positional relationship detection element)
70*b*, 270*b*, 370*b* Projection element
71 Marker member
72 Imaging element
73, 273, 373 Unit side control element (Control element)
90, 290 Irradiation position marker
91, 291 First projection light
92, 292 Second projection light
100, 200, 300 X-ray imaging apparatus
101 Subject
393 Rotation instruction marker
394 Moving instruction marker Also, the inventors intend that only those claims which use the specific and exact phrase "means for" are intended to be interpreted under 35 USC 112. The structure herein is noted and well supported in the entire disclosure. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray imaging apparatus, comprising:

an X-ray irradiation element that irradiates an X-ray to a subject;

an X-ray detection element that detects an X-ray irradiated from said X-ray irradiation element;

an angular relationship detection element that detects a relative angular relationship between a detection surface of said X-ray detection element and an irradiation direction of said X-ray of said X-ray irradiation element; and a projection element that projects an irradiation position marker specifying a position where said X-ray is irradiated from said X-ray irradiation element on a body surface of said subject;

wherein said projection element changes a display mode of said irradiation position marker projected on said body surface of said subject based on a deviation level relative to a preset setting angle of said angular relationship detected by said angular relationship detection element; and wherein said projection element is configured to individually and distinguishably change said display modes of a plurality of irradiation position markers corresponding to each of a plurality of deviation level relatives to said preset setting angles of a plurality of angular relationships in a plurality of rotation directions of said X-ray detection element.

2. The X-ray imaging apparatus, according to claim 1, wherein:

said projection element projects said irradiation position marker indicating a position of an irradiation center of said X-ray irradiated from said X-ray irradiation element on said body surface of said subject, and change said display mode of said irradiation position marker indicating said position of said irradiation center based on said deviation level relative to the setting angle of said angular relationship.

3. The X-ray imaging apparatus, according to claim 1, wherein:

said projection element changes said display mode of said irradiation position marker by switching at least two selected displays from a group consisting of a display, a non-display and a blinking-display of said irradiation position marker projected on said body surface of said subject based on said deviation level relative to said setting angle of said angular relationship detected by said angular relationship detection element.

4. The X-ray imaging apparatus, according to claim 3, wherein:

said angular relationship detection element detects said angular relationship of a first rotation direction, of which a longitudinal axis direction is a rotation axis, and said angular relationship of a second rotation direction, of which a rotation axis is a horizontal axis direction, between said longitudinal axis direction and said horizontal axis direction are orthogonal each other on said detection surface of said X-ray detection element, and said projection element changes individually said display mode of said irradiation position marker relative to a first deviation level and said display mode of said irradiation position marker relative to a second deviation level, wherein each of said first deviation level relative to said setting angle of said angular relationship in said first rotation direction and said second deviation level relative to said setting angle of said angular relationship in said second rotation direction are individually distinguishable one another.

5. The X-ray imaging apparatus, according to claim 4, wherein:

said projection element projects said irradiation position marker having a cruciform indicating a position of said irradiation center of said X-ray irradiated from said X-ray irradiation element by projecting a linear first projection light and a linear second projection light orthogonal each other on said body surface of said subject, and changes said display mode of either projection light of said first projection light or said second projection light based on said first deviation level and in addition changes said display mode of the other rest projection light between said first projection light and said second projection light based on said second deviation level.

6. The X-ray imaging apparatus, according to claim 3, wherein:

said projection element turns said irradiation position marker to non-display when said deviation level relative to said setting angle of said angular relationship detected by said angular relationship detection element is larger than an angle deviation threshold value preliminarily set, and turns said irradiation position marker to display when said deviation level relative to said setting angle of said angular relationship is smaller than said angle deviation threshold value.

7. The X-ray imaging apparatus, according to claim 3, wherein:

said projection element turns said irradiation position marker to the blinking-display when said deviation level relative to said setting angle of said angular relationship detected by said angular relationship detection element is larger than said angler deviation threshold value preliminarily set, and changes a blinking cycle of said irradiation position marker for the blinking-display corresponding to said deviation level relative to said setting angle of said angular relationship.

8. The X-ray imaging apparatus, according to claim 1, wherein:

said setting angle is an orthogonal angle that denotes said angular relationship in which said irradiation direction of said X-ray of said X-ray irradiation element is orthogonal to said detection surface of said X-ray detection element, and said projection element changes said display mode of said irradiation position marker based on the deviation level relative to said orthogonal angle of said angular relationship detected by said angular relationship detection element.

9. The X-ray imaging apparatus, according to claim 1, wherein:

said angular relationship detection element detects said angular relationship in a third rotation direction wherein said orthogonal direction orthogonal to said detection surface of said X-ray detection element is a rotation axis; and said projection element projects a rotation instruction marker on said body surface of said subject to instruct a change of said angular relationship along said third rotation direction and change said display mode of said rotation instruction marker based on said deviation level relative to said setting angle of said angular relationship.

10. The X-ray imaging apparatus, according to claim 1, wherein:

said angular relationship detection element, further comprises:

a marker member installed to said X-ray detection element;

an imaging element that is arranged in said X-ray irradiation element and images optically said marker member; and a control element that detects said angular relationship based on said marker member imaged by said imaging element;

wherein said control element calculates a deviation level relative to said setting angle of said angular relationship based on said detected angular relationship, and changes said display mode of said irradiation position marker projected by said projection element based on said deviation level relative to said setting angle of said calculated angular relationship.

11. The X-ray imaging apparatus, according to claim 10, wherein:

said projection element, said imaging element and said control element are installed on said X-ray irradiation element and demountable.

12. The X-ray imaging apparatus, according to claim 1, further comprising:

a position detection element that detects a relative positional relationship between said X-ray detection element and said X-ray irradiation element;

wherein said projection element projects a moving instruction marker to instruct to change said positional relationship in a direction along said detection surface of said X-ray detection element on said body surface of said subject, and to change said display mode of said moving instruction marker based on a deviation level relative to said preset setting position of said positional relationship detected by said positional relationship detection element.

13. A position determination support unit, for an X-ray imaging apparatus, comprising:

an angular relationship detection element that detects relative angular relationship between an irradiation direction of an X-ray of an X-ray irradiation element that irradiates said X-ray and a detection surface of an X-ray detection element that detects said X-ray irradiated from said X-ray irradiation element; and a projection element that projects an irradiation position marker specifying a position where said X-ray is irradiated from said X-ray irradiation element on a body surface of a subject;

wherein said projection element changes a display mode of said irradiation position marker projected on said body surface of said subject based on a deviation level relative to a preset setting angle of said angular relationship detected by said angular relationship detection element; and wherein said projection element is configured to individually and distinguishably change said display modes of a plurality of irradiation position markers corresponding to each of a plurality of deviation level relatives to said preset setting angles of a plurality of angular relationships in a plurality of rotation directions of said X-ray detection element.

* * * * *